United States Patent
Norman et al.

(10) Patent No.: US 7,354,951 B2
(45) Date of Patent: Apr. 8, 2008

(54) SUBSTITUTED BENZOPYRANS AS SELECTIVE ESTROGEN RECEPTOR-BETA AGONISTS

(75) Inventors: Bryan Hurst Norman, Indianapolis, IN (US); Timothy Ivo Richardson, Zionsville, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 11/574,034

(22) PCT Filed: Oct. 5, 2005

(86) PCT No.: PCT/US2005/035472

§ 371 (c)(1),
(2), (4) Date: Feb. 21, 2007

(87) PCT Pub. No.: WO2006/044176

PCT Pub. Date: Apr. 27, 2006

(65) Prior Publication Data

US 2008/0064742 A1    Mar. 13, 2008

(51) Int. Cl.
*A61K 31/353* (2006.01)
*C07D 311/78* (2006.01)

(52) U.S. Cl. ............................ 514/454; 549/385

(58) Field of Classification Search ............ 549/359, 549/385; 514/454
See application file for complete search history.

(56) References Cited

U.S. PATENT DOCUMENTS 6,630,508 B1    10/2003    Dodge et al.

FOREIGN PATENT DOCUMENTS

| WO | WO 01/64665 | 9/2001 |
| WO | WO 03/044006 | 5/2003 |
| WO | WO 2004/094400 | 11/2004 |
| WO | WO 2004/094401 | 11/2004 |

OTHER PUBLICATIONS

Anderson, et al., "Synthesis of 6,9-bisnormethyl-8-methoxy-12,13-epoxy-6,8,10-trichothec atriene," Journal of Organic Chemistry, vol. 42, No. 6, pp. 1045-1050 (1977).

Oude-Alink, et al., "Photolysis of 2-keto-2,3-dihydrobenzofurans, o-hydroxystyrenes and 1-o-hydroxyphenyl)-1,5-hexadienes," Journal of Organic Chemistry, vol. 38, No. 11, pp. 1993-2001 (1973).

*Primary Examiner*—Bernard Dentz
*Assistant Examiner*—David E Gallis
(74) *Attorney, Agent, or Firm*—John C. Demeter; John A. Cleveland, Jr.

(57) ABSTRACT

The present invention relates to novel benzopyran ER-β agonist compounds, pharmaceutical compositions thereof, and use of these compounds to treat a ER-β mediated disease such as nocturia, obstructive uropathy, benign prostatic hypertrophy, obesity, dementia, hypertension, incontinence, colon cancer, prostate cancer, infertility, depression, leukemia, inflammatory bowel disease, and arthritis. Formula (I), wherein G is —O—, —S(O)$_n$—, —CF$_2$—, —C(O)—, —CR$^1$H— or —CR$^2$(OH)—; R is halo, (C$_1$-C$_4$)alkyl or R$^3$—(CH$_2$)$_m$—; R$^1$ is F, hydroxyl, cyano, trifluoromethyl, (C$_1$-C$_4$)alkyl, (C$_2$-C$_4$)alkenyl, (C$_2$-C$_4$)alkynyl, (C$_1$-C$_4$)alkoxy, (C$_1$-C$_4$)alkylcarbonyloxy or benzyl; R$^2$ is trifluoromethyl or (C$_1$-C$_4$)alkyl; R$^3$ is cyano, hydroxyl, (C$_2$-C$_4$)alkenyl, (C$_1$-C$_4$)alkoxy or (C$_1$-C$_4$)alkoxycarbonyl; n is 0, 1 or 2; and m is 0, 1 or 2; and pharmaceutically acceptable salts thereof.

(I)

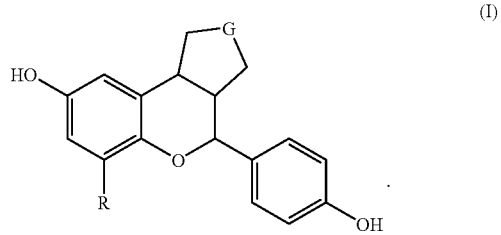

4 Claims, No Drawings

SEQUENCE LISTING

<160> NUMBER OF SEQ ID NOS: 3

<210> SEQ ID NO 1
<211> LENGTH: 19
<212> TYPE: DNA
<213> ORGANISM: Artificial

```
<220> FEATURE:
<223> OTHER INFORMATION: synthetic construct

<400> SEQUENCE: 1
cgcagaccgg actccagat                                                19

<210> SEQ ID NO 2
<211> LENGTH: 19
<212> TYPE: DNA
<213> ORGANISM: Artificial
<220> FEATURE:
<223> OTHER INFORMATION: synthetic construct

<400> SEQUENCE: 2
ccacgcacag caggagaat                                                19

<210> SEQ ID NO 3
<211> LENGTH: 21
<212> TYPE: DNA
<213> ORGANISM: Artificial
<220> FEATURE:
<223> OTHER INFORMATION: synthetic construct

<400> SEQUENCE: 3
ccaaggaggc cacgccatga a                                             21
```

SUBSTITUTED BENZOPYRANS AS SELECTIVE ESTROGEN RECEPTOR-BETA AGONISTS

BACKGROUND OF THE INVENTION

The present invention relates to novel benzopyran ER-β agonist compounds, pharmaceutical compositions thereof, and use of these compounds to treat a ER-β mediated disease such as benign prostatic hypertrophy, obesity, dementia, hypertension, incontinence, colon cancer, prostate cancer, infertility, depression, leukemia, inflammatory bowel disease, and arthritis.

Estrogens play important roles in the development and homeostasis of the reproductive, central nervous, skeletal, and cardiovascular systems of both males and females. Recently, a new estrogen receptor ("ER") isoform, ER-β is cloned from a rat prostatic cDNA library and is present in murine and human prostates. Consequently, the previously known ER is now designated as ER-α. ER-α and ER-β share high amino acid homology, have similar 17-β Estradiol (E2) binding affinities, and can hetero- or homodimerize to form a signaling complex. See, e.g., Kuiper G G, et al., Endocrinol. 138: 863-70 (1997); and Kuiper G G et al., Proc. Natl. Acad. Sci. USA 93: 5925-30 (1996). Although E2 activates both ER-α and ER-β, tissue distribution and functional differences between the two have been noted, making subtype selective ligands more attractive for various disease targets. Interestingly, 3-beta, 17-beta-androstanediol and 5-alpha-androstane have been proposed to be endogenous ligands for ER-β. See e.g., Weihua Z. et al. PNAS 98: 6330-5 (2001). 3-Beta, 17-beta-androstanediol is a major metabolite of dihydrotestosterone (DHT), the 5-alpha-reduced active intracellular androgen in male accessory sex organs. ER-β activation also stimulates increased glutathione S-transferase and quinone reductase expression. These two enzymes have been shown to possess chemoprotective detoxification properties; Chang W Y et al., Prostate 40: 115-24 (1999); Montano M M et al., J. Biol. Chem. 273: 25443-9 (1998).

With the recent identification of ER-β, and the recognition that ER-α and ER-β have different biological roles, ER-selective modulators would similarly possess significant clinical utility. Since ER-β is strongly expressed in a number of tissues including prostate, bladder, ovary, testis, lung, small intestine, vascular endothelium, and various parts of the brain, compounds that selectively modulate ER-β have been suggested as being useful in the treatment of a variety of disease conditions, such as obesity, dementia, hypertension, incontinence, colon cancer, prostate cancer, infertility, depression, leukemia, inflammatory bowel disease, and arthritis. See e.g., J. Gustafsson, TIPS, 24 (9), p 479-485 (2003); and Endocrinology, 144, p. 4241-4249 (2003). Selective compounds should have minimal effect on tissues that contain ER-α, and thus exhibit different side-effect profiles. Thus, ER-β agonists will display different therapeutic profiles compared to ER-α antagonists or agonists, and would be preferentially beneficial in tissues relying on ER-β signaling.

The prostate gland produces components that are found in the semen and blood. Some of these are regulatory peptides. The prostate gland comprises stroma and epithelium cells, the latter group consisting of columnar secretory cells and basal non-secretory cells. The proliferation of these basal cells, as well as stroma cells gives rise to benign prostatic hyperplasia (BPH), which is one common prostate disease. BPH is a progressive condition that is characterized by the nodular enlargement of the prostatic tissue resulting in obstruction of the urethra. This results in increased frequency of urination, noncuria, poor urine stream, and hesitation or delay in starting the urine flow. Consequences of BPH can include hypertrophy of bladder smooth muscle, decompensated bladder, and increased incidence of urinary tract infection. The development of BPH is considered to be an inescapable phenomenon for the aging male population. BPH is observed in approximately 70% of males over the age of 70. Drug treatment for BPH currently employs alpha andrenergic antagonists for symptomatic relief or steroid 5-alpha reductase inhibitors to reduce hyperplastic tissue bulk. Because these approaches are of limited therapeutic benefit, new therapies are needed.

BRIEF SUMMARY OF THE INVENTION

In a 1$^{st}$ embodiment, the present invention provides a compound of Formula I:

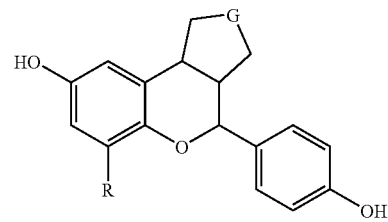

wherein:

G is —O—, —S(O)$_n$—, —CF$_2$—, —C(O)—, —CR$^1$H— or —CR$^2$(OH)—;

R is halo, (C$_1$-C$_4$)alkyl or R$^3$—(CH$_2$)$_{m-1}$;

R$^1$ is F, hydroxyl, cyano, trifluoromethyl, (C$_1$-C$_4$)alkyl, (C$_2$-C$_4$)alkenyl, (C$_2$-C$_4$)alkynyl, (C$_1$-C$_4$)alkoxy, (C$_1$-C$_4$)alkylcarbonyloxy or benzyl;

R$^2$ is trifluoromethyl or (C$_1$-C$_4$)alkyl;

R$^3$ is cyano, hydroxyl, (C$_2$-C$_4$)alkenyl, (C$_1$-C$_4$)alkoxy or (C$_1$-C$_4$)alkoxycarbonyl;

n is 0, 1 or 2; and m is 0, 1 or 2;

and pharmaceutically acceptable salts thereof.

In a specific embodiment of the compound of Formula I:

G is —CF$_2$— or —C(O)—;

R is halo, methyl, ethyl or R$^3$—(CH$_2$)$_m$—;

R$^3$ is cyano, hydroxyl, vinyl, methoxy or ethoxy; and m is 0 or 1.

In a specific embodiment of the compound of Formula I:

G is —CF$_2$—;

R is halo, methyl, ethyl or R$^3$—(CH$_2$)$_m$—;

R$^3$ is cyano, hydroxyl, vinyl, methoxy or ethoxy; and m is 0 or 1.

In another specific embodiment of the compound of Formula I:

G is —CF$_2$— or —C(O)—;

R is halo, methyl or R$^3$—(CH$_2$)$_m$—;

R$^3$ is cyano, hydroxyl, vinyl or methoxy; and m is 0 or 1.

In another specific embodiment of the compound of Formula I: G is —CF$_2$— or C(O)— and R is halo, hydroxyl, cyano, methyl, methoxymethyl, cyanomethyl, hydroxymethyl or vinyl.

In another specific embodiment of the compound of Formula I: G is —CF$_2$— and R is methyl or methoxymethyl.

In another specific embodiment, the compound of Formula I is selected from the group consisting of:

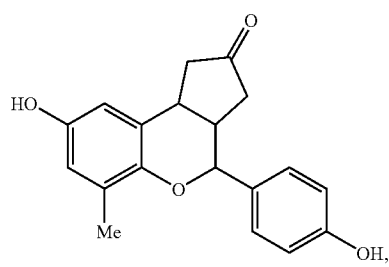

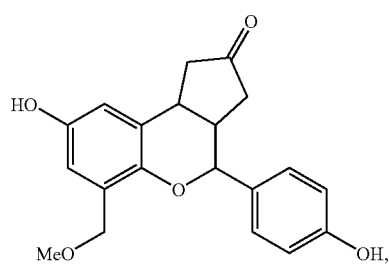

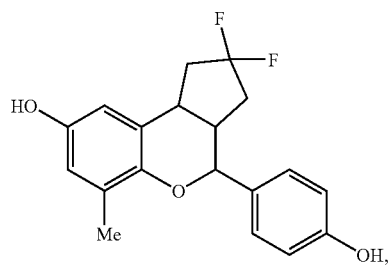

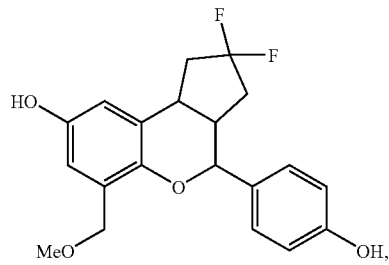

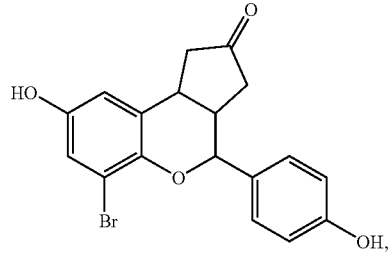

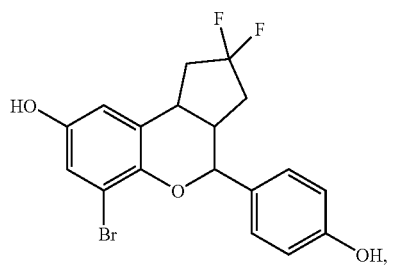

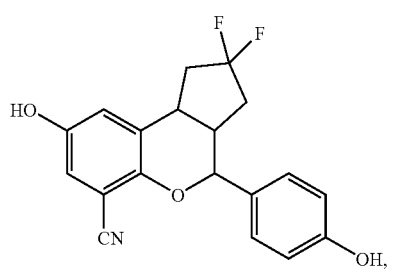

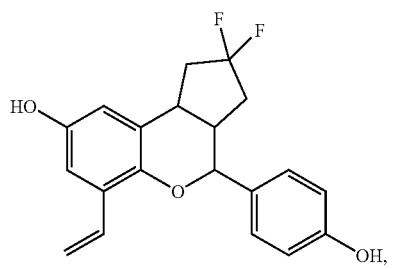

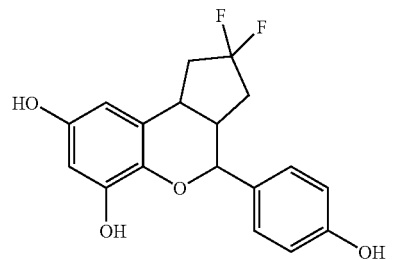

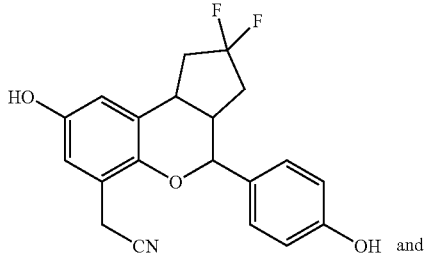

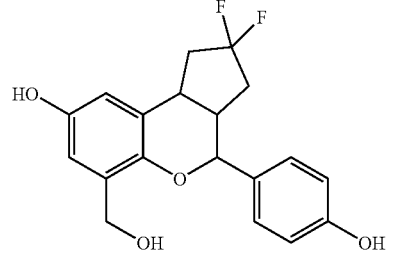

and including all racemic mixtures and specific enantiomers thereof.

In a 2$^{nd}$ embodiment, the present invention provides a pharmaceutical composition comprising: a compound of Formula I, or pharmaceutically acceptable salt thereof, together with a pharmaceutically acceptable carrier, diluent or excipient.

In a 3$^{rd}$ embodiment, the present invention provides a method of treating nocturia, obstructive uropathy, obesity, dementia, hypertension, incontinence, colon cancer, prostate cancer, infertility, depression, leukemia, inflammatory bowel disease, arthritis, or benign prostatic hypertrophy in a patient, comprising: administering to said patient an effective amount of a compound of Formula I, or pharmaceutically acceptable salt thereof.

In a specific embodiment, the condition being treated is benign prostatic hypertrophy.

In another specific embodiment, the condition being treated is prostate cancer.

In a 4$^{th}$ embodiment, the present invention provides a method of treating nocturia, uropathy, obesity, dementia, hypertension, incontinence, colon cancer, prostate cancer, infertility, depression, leukemia, inflammatory bowel disease, arthritis or benign prostatic hypertrophy in a patient, comprising: administering to said patient a pharmaceutical composition comprising a compound of Formula I, or pharmaceutically acceptable salt thereof, together with a pharmaceutically acceptable carrier, diluent or excipient.

In a specific embodiment, the condition being treated is benign prostatic hypertrophy.

In another specific embodiment, the condition being treated is prostate cancer.

In a 5$^{th}$ embodiment, the present invention provides the use of a compound, or pharmaceutically acceptable salt thereof, of Formula I for the manufacture of a medicament for the treatment of nocturia, uropathy, obesity, dementia, hypertension, incontinence, colon cancer, prostate cancer, infertility, depression, leukemia, inflammatory bowel disease, arthritis, or benign prostatic hypertrophy.

In a specific embodiment, the medicament is for the treatment of benign prostatic hypertrophy.

In another specific embodiment, the medicament is for the treatment of prostate cancer.

In a 6$^{th}$ embodiment, the present invention provides a method of agonizing ER-β receptor function, comprising: contacting the receptor with a compound of Formula I, or a pharmaceutically acceptable salt thereof.

In a 7$^{th}$ embodiment, the present invention provides a method of agonizing ER-β receptor function in a patient, comprising: administering to said patient an effective amount of a compound of Formula I, or a pharmaceutically acceptable salt thereof.

In an 8$^{th}$ embodiment, the present invention provides a method of treating ER-β mediated disease condition in a patient, comprising: administering to said patient an effective amount of a compound of Formula I, or a pharmaceutically acceptable salt thereof.

In a specific embodiment, the condition is nocturia, obstructive uropathy, obesity, dementia, hypertension, incontinence, colon cancer, prostate cancer, infertility, depression, leukemia, inflammatory bowel disease, arthritis, or benign prostatic hypertrophy.

In another specific embodiment, the condition is benign prostatic hypertrophy.

In another specific embodiment, the condition is prostate cancer.

DETAILED DESCRIPTION OF THE INVENTION

As used herein:

a) the term "$C_1$-$C_4$ alkyl" refers to a branched or straight chained alkyl radical containing from 1 to 4 carbon atoms, such as, but not limited to methyl (Me), ethyl (Et), n-propyl, isopropyl, n-butyl, isobutyl, sec butyl (s-Bu) or tert-butyl (t-Bu);

b) the term "$C_2$-$C_4$ alkenyl" refers to a straight or branched hydrocarbon chain of 2 to 4 carbon atoms with at least one carbon-carbon double bond. Examples of $C_2$-$C_4$ alkenyl groups include, but are not limited to, ethenyl (vinyl), propen-1-yl, propen-2-yl (isoprenyl), propen-3-yl (allyl), 2-methyl-propen-3-yl, 2-buten-4-yl, 2-methyl-propen-1-yl, and 1-buten-1-yl;

c) the term "$C_2$-$C_4$ alkynyl" refers to a straight or branched hydrocarbon chain of 2 to 4 carbon atoms with at least one carbon-carbon triple bond. Examples of $C_2$-$C_4$ alkynyl groups include, but are not limited to, ethynyl, propyn-1-yl, propyn-2-yl (isoprynyl), propyn-3-yl, 2-methyl-propyn-3-yl, 2-butyn-4-yl, 2-methyl-propyn-1-yl, and 1-butyn-1-yl;

d) the term "halide" refers to a fluorine atom, chlorine atom, bromine atom, or iodine atom;

e) the designation "" refers to a bond for which the stereochemistry is not designated;

f) the designation "" refers to a bond that protrudes forward out of the plane of the page;

g) the designation "" refers to a bond that protrudes backward out of the plane of the page;

h) as used in the preparations and examples the following terms have the indicated meanings; "ng" refers to nanograms; "µg" refers to micrograms; "mg" refers to milligrams; "g" refers to grams; "kg" refers to kilograms; "nmole" refers to nanomoles; "mmol" refers to millimoles; "mol" refers to moles; "µL" refers to microliters; "mL" refers to milliliters; "L" refers to liters: "$R_f$" refers to retention factor; "° C." refers to degrees Celsius; "bp" refers to boiling point; "mm of Hg" refers to pressure in millimeters of mercury; "mp" refers to melting point; "dec" refers to decomposition; "$[\alpha]^2_D{}^0$" refer to specific rotation of the D line of sodium at 20° C. obtained in a 1 decimeter cell; "c" refers to concentration in g/mL; "nM" refers to nanomolar; "µM" refers to micromolar; "mM" refers to millimolar; "M" refers to molar; "$K_i$" refers to inhibition constant; "$K_d$" refers to dissociation constant; "psi" refers to pounds per square inch; "rpm" refers to revolutions per minute; "HPLC" refers to high performance liquid chromatography; "HRMS" refers to high resolution mass spectrum; "THF" refers to tetrahydrofuran; "brine" refers to a saturated aqueous solution of sodium chloride; "L.O.D." refers to loss on drying; "µCi" refers to microcuries; "i.p." refers to intraperitoneally; "i.v." refers to intravenously; and "DPM" refers to disintegrations per minute; and i) the term "enantiomeric excess" or "ee" refers to the percent by which one enantiomer, E1, is in excess in a mixture of the two enantiomers, E1 plus E2, such that {(E1−E2)÷(E1+E2)}×100=ee;

j) the term "patient" refers to a warm blooded animal such as a mammal that is afflicted with a particular estrogen receptor-beta mediated disease. It is understood that guinea pigs, dogs, cats, rats, mice, horses, cattle, sheep, and humans are examples of animals within the scope of the meaning of the term;

k) the terms "effective amount" and "therapeutically effective amount" of a compound of Formula (I) refer to an amount which is effective in controlling diseases and conditions associated with estrogen receptor-beta mediated diseases such as obesity, dementia, hypertension, incontinence, colon cancer, prostate cancer, infertility, depression, leukemia, inflammatory bowel disease, arthritis or benign prostatic hypertrophy;

l) the term "controlling diseases" is intended to refer to all processes wherein there may be a slowing, interrupting, arresting, or stopping of the progression of the diseases and conditions described herein, but does not necessarily indicate a total elimination of all disease and condition symptoms, but does include prophylactic treatment of the diseases and conditions associated with estrogen receptor-beta mediated diseases such as obesity, dementia, hypertension, incontinence, colon cancer, prostate cancer, infertility, depression, leukemia, inflammatory bowel disease, arthritis or benign prostatic hypertrophy;

m) the term "pharmaceutically acceptable salts thereof" refers to either an acid addition salt or a basic addition salt;

n) the term "pharmaceutically acceptable acid addition salts" is intended to apply to any non-toxic organic or inorganic acid addition salt of the base compounds represented by formula (I). Illustrative inorganic acids that form suitable salts include hydrochloric, hydrobromic, sulphuric, and phosphoric acid and acid metal salts such as sodium monohydrogen orthophosphate, and potassium hydrogen sulfate. Illustrative organic acids that form suitable salts include the mono-, di-, and tricarboxylic acids. Illustrative of such acids are for example, acetic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salicyclic, 2-phenoxy-benzoic, p-toluenesulfonic acid, and sulfonic acids such as benzenesulfonic acid, methanesulfonic acid, and 2-hydroxyethanesulfonic acid. Such salts can exist in either a hydrated or substantially anhydrous form. In general, the acid addition salts of these compounds are soluble in water and various hydrophilic organic solvents, and which in comparison to their free base forms, generally demonstrate higher melting points.

o) the term "pharmaceutically acceptable basic addition salts" is intended to apply to any non-toxic organic or inorganic basic addition salts of the compounds represented by formula (I). Illustrative bases which form suitable salts include alkali metal or alkaline-earth metal hydroxides such as sodium, potassium, calcium, magnesium, or barium hydroxides; ammonia, and aliphatic, alicyclic, or aromatic organic amines such as methylamine, dimethylamine, trimethylamine, and picoline. Either the mono- or di-basic salts can be formed with those compounds.

Compounds of Formula I may have one or more asymmetric centers. As a consequence of these chiral centers, the compounds of the present invention occur as racemates and as individual enantiomers, as well as diastereomers and mixtures of diastereomers. All asymmetric forms, individual isomers and combinations thereof, are within the scope of the present invention.

In order to preferentially prepare one optical isomer over its enantiomer, a number of routes are available. As an example, a mixture of enantiomers may be prepared, and then the two enantiomers may be separated. A commonly employed method for the separation of a racemic mixture is the use of chiral high pressure liquid chromatography. Further details regarding resolution of enantiomeric mixtures may be found in J. Jacques, et al., Enantiomers, Racemates, and Resolutions, (1991).

Reaction Schemes

Compounds of Formula I, and intermediates thereof, can be prepared as described in Reaction Schemes 1-6 below. All substituents, unless otherwise indicated, are as previously defined. The reagents and starting materials are readily available to one of ordinary skill in the art.

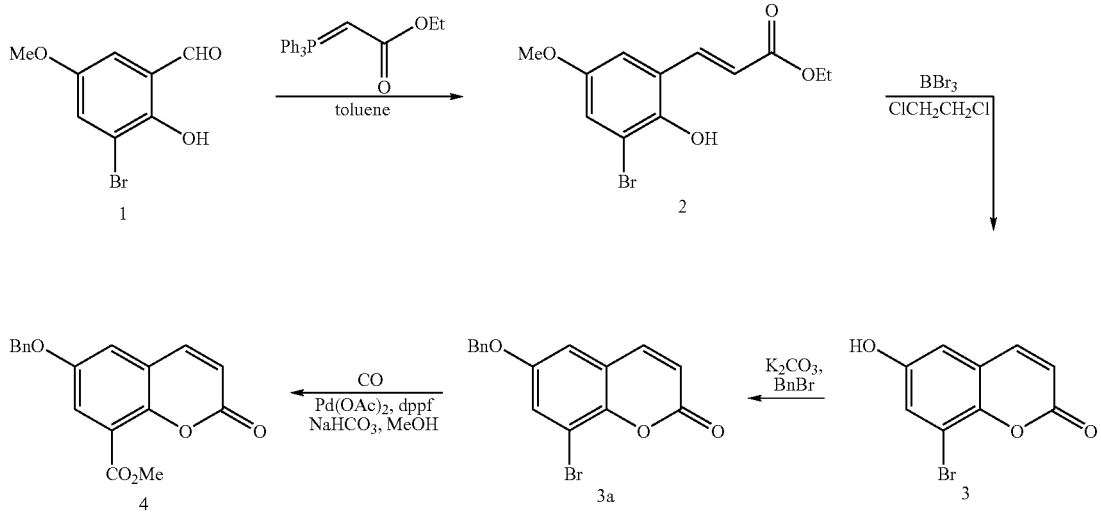

Scheme 1

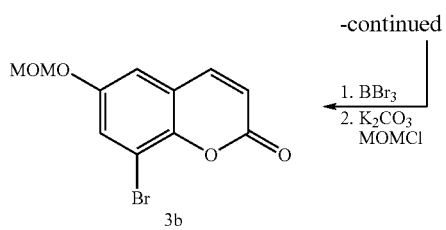

The bromide 1, prepared in a manner similar to that described by Rubenstein, L. *J. Chem. Soc, Abstracts* 1925, 127, 1998-2004, is reacted with (carbethoxymethylene)triphenylphosphorane to form the α,β-unsatutrated ester 2. The α,β-unsatutrated ester 2 is reacted with boron tribromide (BBr₃) with heating in dichloroethane to form the coumarin 3. The phenolic hydroxyl of coumarin 3 can be protected as the benzyl ether using potassium carbonate (K₂CO₃) in the presence of benzyl bromide to give 3a. The benzyl protecting group of 3a can be exchanged for methoxymethyl ether by treating 3a with boron tribromide to give back unprotected coumarin 3 followed by reaction with potassium carbonate in the presence of chloromethyl methyl ether (MOMCl) to give 3b. The benzyl protected coumarin 3a is reacted with carbon monoxide in the presence of palladium acetate [Pd(OAc)₂)], 1,1'-bis(diphenylphosphino)ferrocene (dppf), sodium bicarbonate (NaHCO₃) and methanol (MeOH) to from 8-carboxycoumarin 4.

propyl phosphite [P(OiPr)₃] (Trost, B. M. *Angew. Chem. Int. Ed. Engl.* 1986, 25, 1-20). The enol triflate of 5 is then formed by deprotonating 5 with an appropriate base, as known by one skilled in the art, such as lithium bis(trimethylsilyl)amide (LiHMDS) followed by trapping the enolate with N-(5-chloro-2-pyridyl)triflimide in an appropriate solvent, such as THF. The enol triflate is coupled with lithiated p-benzyloxybromobenzene using Negishi conditions; zinc chloride (ZnCl₂) and palladium-tetrakis triphenylphosphine [Pd(PPh₃)₄], in an appropriate solvent, such as THF (Negishi, E. *Acc. Chem. Res.* 1982, 15, 340-348) to give flavene 6. The enol of flavene 6 is reduced with triethyl silane (Et₃SiH) in the presence of trifluoroacefic acid (TFA) to give flavan 7. The carboxy group of flavan 7 is reduced with lithium aluminum hydride to give a benzyl alcohol that is reacted with sodium hydride and methyl iodide to give the

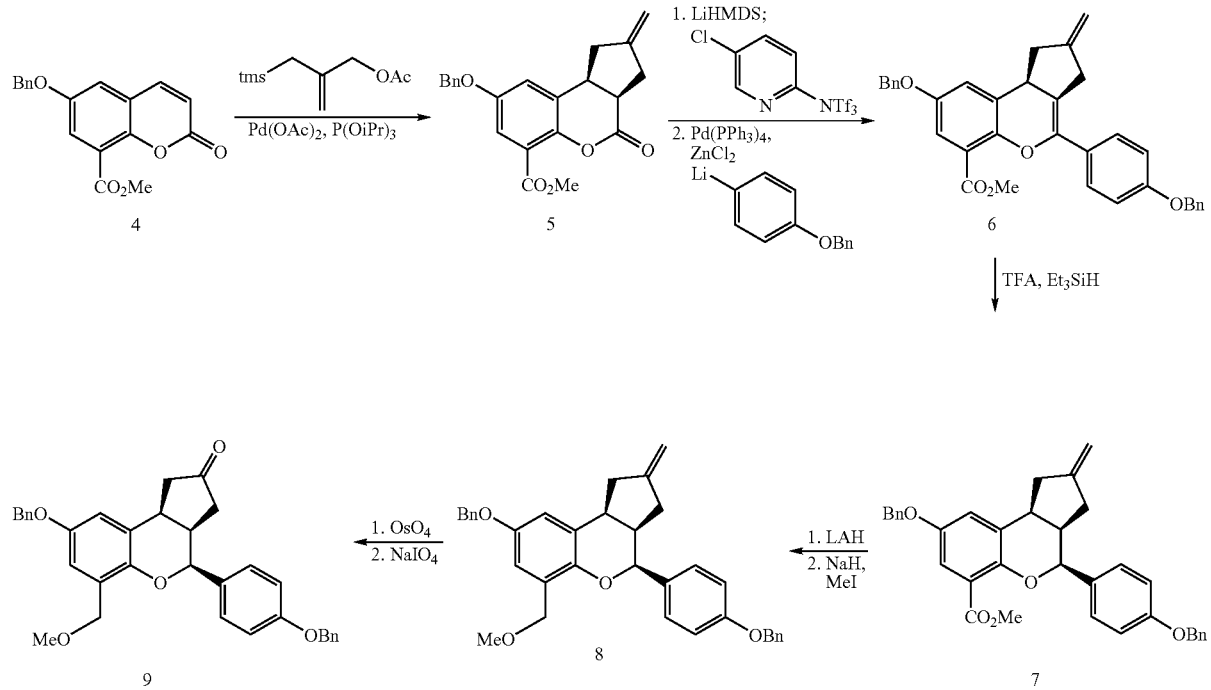

In Scheme 2, the cyclopentanoid 5 is formed via [3+2] cycloaddition to 6-benzyloxy-8-carboxycoumarin 4 using Trost's trimethylenemethane chemistry; 2-(acetyoxymethyl)allyl-triethylsilane, palladium acetate [Pd(OAc)₂] and triisomethyl ether 8. The exomethylene of 8 is dihydroxylated using osmium tetroxide (OsO₄) and N-methylmorpholine-N-oxide (NMO) followed by oxidative cleavage of the diol with an appropriate oxidant such as sodium periodate (NaIO₄) in one pot to give the cyclopentanone 9.

Scheme 3

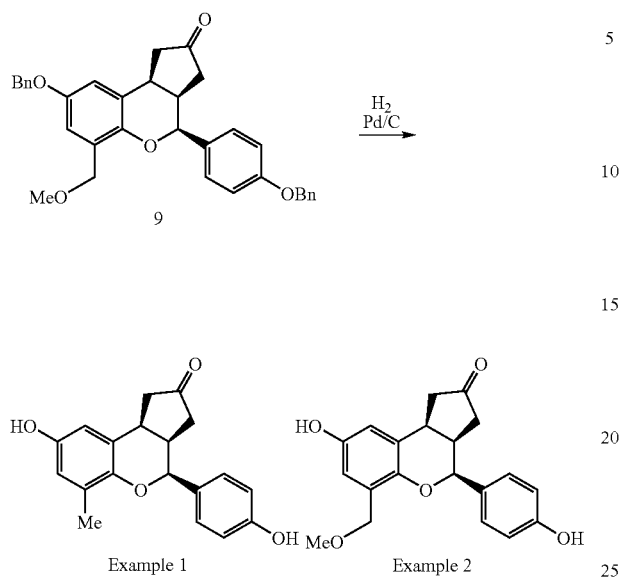

In Scheme 3, the benzyl groups of cyclopentanone 9 are removed by hydrogenolysis using hydrogen ($H_2$) in the presence of palladium on carbon (Pd/C) to give Examples 1 and 2.

In Scheme 4, the bromo substituted benzopyran 14 is prepared from methoxymethyl ether protected coumarin 3b in a manner substantially similar the route described in Scheme 2. The benzopyran 14 is treated with DAST to form the difluoro analog 15.

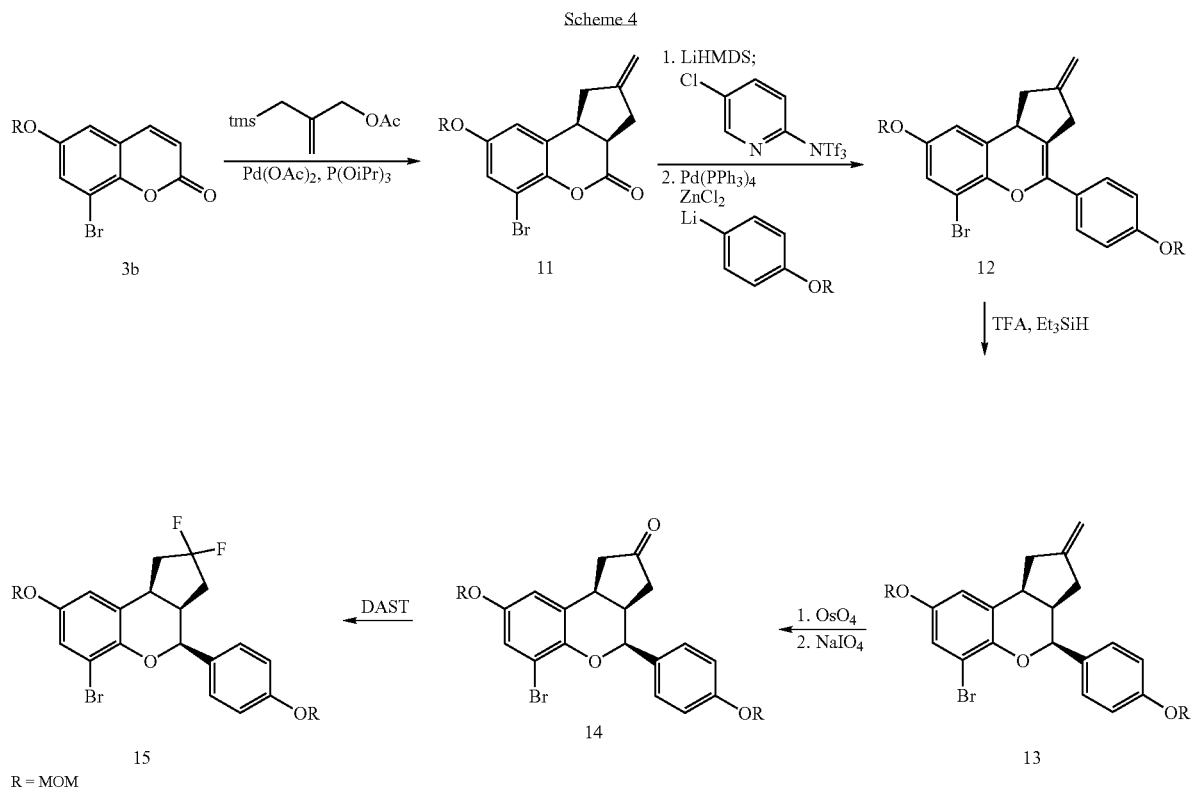

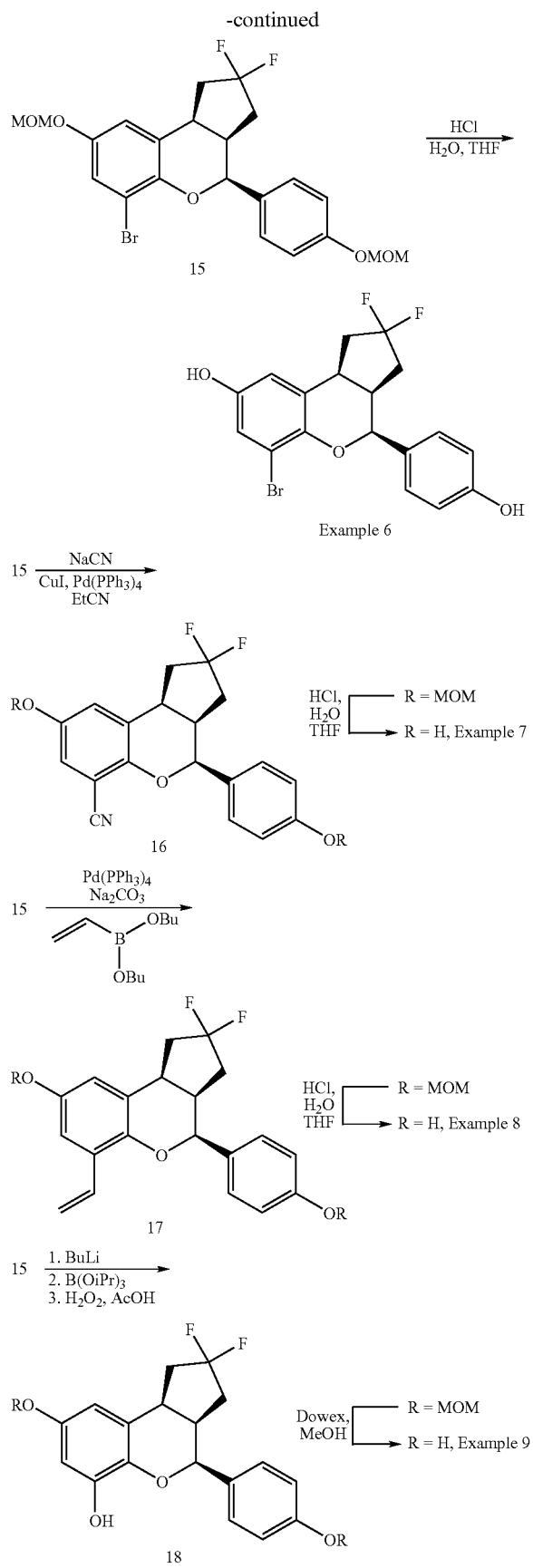
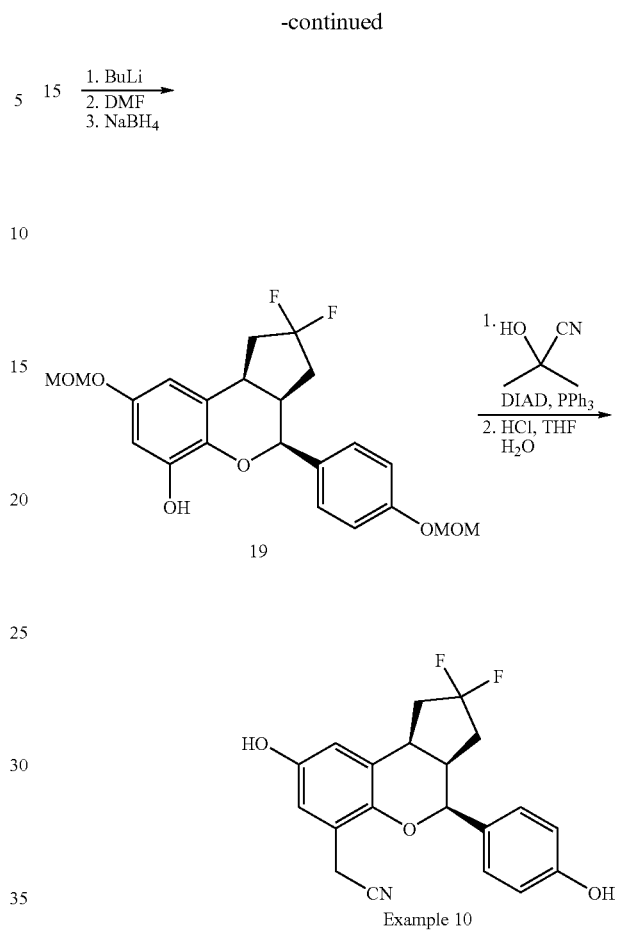

In Scheme 5, bromo substituted benzopyran 14 is treated with hydrogen chloride in water and THF to give Example 5. The difluoro-analog 15 is treated in a similar manner to give Example 6. Difluorobromobenzopyran 15 is reacted with sodium cyanide in the presence of copper(I) iodide (CuI), and $Pd(PPh_3)_4$, in an appropriate solvent, such as propionitrile, to give cyano substituted benzopyran 16 which is deprotected with hydrogen chloride in water and THF to give Example 7. Difluorobromobenzopyran 15 is reacted with vinylboronic acid dibutyl ester, sodium carbonate ($Na_2CO_3$), and $Pd(PPh_3)_4$ to give vinyl substituted benzopyran 17 which is deprotected with hydrogen chloride in water and THF to give Example 8. Difluorobromobenzopyran 15 is reacted with butyllithium (BuLi) followed by triisopropyl borate [$B(OiPr)_3$] followed by oxidatation with hydrogen peroxide ($H_2O_2$) to give hydroxy substituted benzopyran 18 which is deprotected with Dowex® acidic resin in methanol to give Example 9. Difluorobromobenzopyran 15 is reacted with butyllithium followed by dimethyl formamide (DMF) followed by reduction with sodium borohydride ($NaBH_4$) to give benzyl alcohol 19. The benzyl alcohol of 19 is reacted with cyanide using acetone cyanohydrin under appropriate Mitsunobu conditions (Mitsunobu, O, Synthesis 1981, 1-28) followed by deprotection with hydrogen chloride in water and THF to give Example 10.

Scheme 6

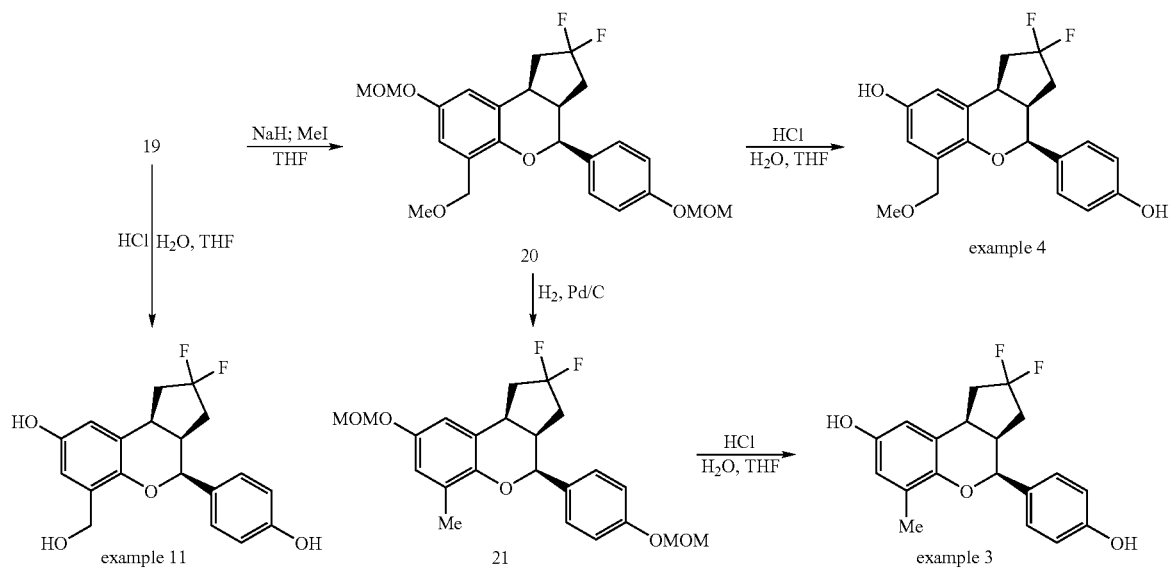

In Scheme 6, alcohol of 19 can be reacted with sodium hydride followed by methyl iodide to give methyl ether 20. Deprotection of 20 with hydrogen chloride in water and THF gives Example 4. The methyl ether of 20 can also be removed under reductive conditions using hydrogen ($H_2$) in the presence of palladium on carbon (Pd/C) to give the methyl substituted compound 21. Deprotection of 21 with hydrogen chloride in water and THF gives Example 3. Deprotection of 19 with hydrogen chloride in water and THF gives Example 11.

PREPARATION 1

(E)-3-(3-Bromo-2-hydroxy-5-methoxy-phenyl)-acrylic acid ethyl ester (2)

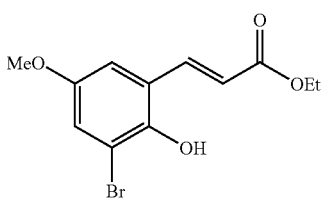

Prepare bromide 1 in a manner similar to that described by Rubenstein, L. *J. Chem. Soc, Abstracts* 1925, 127, 1998-2004. Dissolve the bromide 1 (100 g, 432.81 mmol) in 2 L of toluene. Add (carbethoxymethylene)-triphenylphosphorane (158.32 g, 454.45 mmol), flush with $N_2$, allow to stir at RT 1 hour. Remove volatiles iv, add $Et_2O$, concentrate down until ppt. forms, filter, rinse with $Et_2O$ and civ the filtrate to yield 227 g of a dark oil. Purify by flash chromatography (2 kg of silica gel, 10% EtOAc/hexane to remove forerun then 15% EtOAc/hexane for product) to yield 111 g (85%) of preparation 1. NMR ($CDCl_3$) δ 7.89 (d, J=16.1 Hz, 1H), 7.07 (d, J=2.9 Hz, 1H), 6.98 (d, J=2.9 Hz, 1H), 6.54 (d, J=16.1 Hz, 1H), 5.6 (s, 1H), 4.27 (q, J=7.2 Hz, 2H), 3.77 (s, 3H), 1.35 (t, J=7.2 Hz, 3H).

PREPARATION 2

8-Bromo-6-hydroxy-chromen-2-one (3)

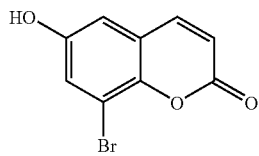

Charge a 12 L, 3-neck flask, fitted with condenser and hooked to a 5 M NaOH trap with preparation 1 (111 g, 368.60 mmol) and dichloroethane (6 L). Add $BBr_3$ (387.87 g, 146.36 mL, 1.55 mol) via a dropping funnel. Heat to 60° C. and let stir overnight. Cool to 0° C. and carefully add MeOH until a homogenous solution occurs. Warm to room temperature and civ. Add $CH_2Cl_2$ to form a dark solution and a dark brown solid occur. Filter the solid and civ the filtrate to yield 32.1 g of a dark brown solid from the filtrate and 53.2 g of a dark purple solid that can be filtered off. The first solid from the filtrate is the hydrolyzed acid from starting material. The second solid that is originally filtered off is desired product. Resubmit the 32 g batch to the reaction conditions. Combine all crude batches, add EtOAc, filter, rinse and vacuum dry to yield 55.6 g of a purple solid. Concentrate the filtrate and triturate with $Et_2O$, filter and dry to yield an additional 11.3 g of a dark brown solid. Total yield from both crops is 66.9 g (75%) of preparation 2. NMR (DMSO-$d_6$) δ 10.2 (bds, 1H), 7.95 (d, J=9.3 Hz, 1H), 7.26 (d, J=2.6 Hz, 1H), 7.04 (d, J=3.1 Hz, 1H), 6.47 (d, J=9.7 Hz, 1H); LRMS (ES−) 238.9 (M−1).

PREPARATION 3

6-Benzyloxy-8-bromo-chromen-2-one (3a)

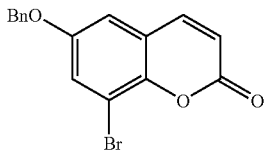

Dissolve preparation 2 (66.5 g, 275.89 mmol) in 1.5 L of dry DMF. Add finely powdered (325 mesh) $K_2CO_3$ (91.56 g, 662.13 mmol) followed by benzyl bromide (56.63 g, 331.07 mmol). Stir rapidly at room temperature overnight. Add 2 L of EtOAc, wash with $H_2O$ (1×2 L), 10% LiCl (3×, 4 L total volume) and brine. Dry over $Na_2SO_4$, filter and civ to yield a brown solid. Dissolve in hot EtOAc (2 L), filter off an insoluble brown solid, add hexane (~500 mL) and allow to cool slowly, overnight. Filter off the resultant brown solid. This yields 50.3 g of a dark brown material. A second crop crashes out of the filtrate. This yields 8.1 g of a tan solid. Reduce the filtrate volume to ~500 mL and placed on a plug of silica gel (1 kg, eluted with 1:1 EtOAc/hexane) to yield an additional 14.9 g of a darker brown solid. The total combined yield is 73.3 g (80%) of preparation 3. NMR (DMSO-$d_6$) δ 7.96 (d, J=9.2 Hz, 1H), 7.58 (d, J=2.6 Hz, 1H), 7.45-7.32 (m, 6H), 6.53 (d, J=9.7 Hz, 1H), 5.15 (s, 2H).

PREPARATION 4

6-Benzyloxy-2-oxo-2H-chromene-8-carboxylic acid methyl ester (4)

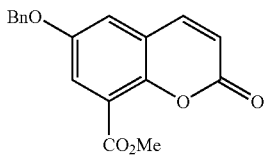

Load a pressure flask with preparation 3 (33 g, 99.65 mmol), Pd(OAc)$_2$ (2.24 g, 9.96 mmol), dppf (6.63 g, 11.96 mmol) and NaHCO$_3$ (10.5 g, 119.58 mmol). Flush with $N_2$, add MeOH (525 mL) then DMSO (350 mL), flush with $N_2$ again, then CO at 30 psi. Warm to 80° C., pressure goes to 30 psi. Let stir 24 hours, material slowly goes into solution. Let cool and stir overnight. Crystals form. Filter off crystals, wash with EtOAc, combine filtrates, remove most of the MeOH, dilute with EtOAc, wash 3× with $H_2O$, brine, dry over $Na_2SO_4$, filter, concentrate and combine with crystals. Pass the dark brown solid through a plug of silica gel (1 kg, 1:1 EtOAc/hexane elution) to obtain an orange solid. Recrystallize from $CH_2Cl_2$/hexane (several crops) to yield 23.1 g (75%) of preparation 4. NMR (DMSO-$d_6$) δ 8.01 (d, J=9.7 Hz, 1H), 7.6 (m, 2H), 7.46 (m, 2H), 7.4-7.35 (m, 2H), 7.34 (m, 1H), 6.55 (d, J=9.7 Hz, 1H), 5.18 (s, 2H), 3.88 (s, 3H); LRMS (ES+) 311.04 (M+1).

PREPARATION 5

8-bromo-6-methoxymethoxy-2-oxo-2H-chromene (3b)

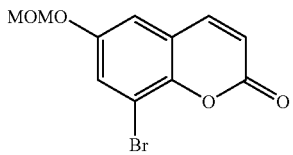

Add BBr$_3$ (0.75 mL, 8 mmol) to preparation 3(662 mg, 2.0 mmol) in 20 mL of dichloromethane at 0° C. Let stir for 15 min. Add 8 mL of methanol and then concentrate. Adsorb to 6 g of silica gel and purify by flash chromatography (40 g, 10-50% A/B, A=10% MeOH in EtOAc, B=hexanes) to give 476 mg of 8-Bromo-6-hydroxy-chromen-2-one (3). Add chloromethyl methyl ether (0.18 mL) to a solution of 8-bromo-6-hydroxy-chromen-2-one (476 mg, 1.97 mmol) and K$_2$CO$_3$ (660 mg, 4.77 mmol) in 10 of DMF. Let the solution stir overnight, add 0.09 mL more chloromethyl methyl ether, let stir 2 hrs, dilute with EtOAc, wash with water, 1:1 water:brine, brine, dry (Na$_2$SO$_4$), filter and concentrate to yield 524 mg (1.84 mmol, 93%) of preparation 5. $^1$H NMR (400 MHz, CDCl$_3$) δ 7.63 (d, 1H, J=9.2 Hz), 7.50 (d, 1H, J=2.6 Hz), 7.12 (d, 1H, J=2.6 Hz), 6.46 (d, 1H, J=9.7 Hz), 5.20 (s, 2H), 3.50 (s, 3H).

PREPARATION 6

8-Benzyloxy-2-methylene-4-oxo-1,2,3,3a,4,9b-hexahydro-cyclopenta[c]chromene-6-carboxylic acid methyl ester (5)

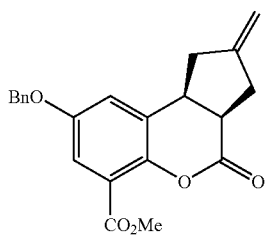

To a solution of preparation 4 (198 mg, 0.64 mmol) and Pd(OAc)$_2$ (17 mg, 0.076 mmol) in 4 mL THF add 2-(acetoxymethyl)allyl-trimethylsilane (0.163 mL, 0.122 mmol) followed by triisopropyl phosphite (0.12 mL, 0.49 mmol). After stirring at 60° C. overnight, cool the solution to room temperature, concentrate under reduced pressure, and dilute with EtOAc. Wash the solution with saturated aqueous sodium bicarbonate and brine. Dry over Na$_2$SO$_4$, and then concentrate to an oil. Purify the material by silica gel chromatography (10 g, 10 to 30% EtOAc/Hex over 30 min at 35 mL/min) to give 80 mg (0.208 mol, 63%) of preparation 6 and 30 mg (0.091 mmol, 27%) of recovered starting material. $^1$H NMR (400 MHz, CDCl$_3$) δ 7.48-7.36 (m, 6H), 7.01 (d, 1H, J=3.1 Hz), 5.10 (s, 2H), 5.01 (m, 2H), 3.97 (s, 3H), 3.43 (dt, 1H, J=7.5, 3.1 Hz), 3.21-3.10 (m, 2H), 2.86-2.74 (m, 2H), 2.43 (m, 1H).

PREPARATION 7

8-Benzyloxy-4-(4-benzyloxy-phenyl)-2-methylene-1,2,3,9b-tetrahydro-cyclopenta[c]chromene-6-carboxylic acid methyl ester (6)

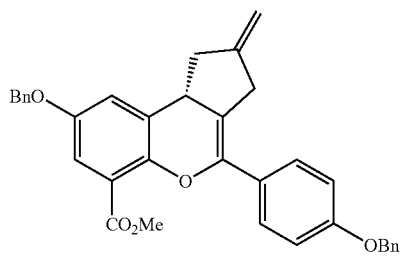

To a solution of p-benzyloxybromobenzene (2.17 g, 8.25 mmol) in 82 mL of THF at −78° C. add t-BuLi (9.7 mL of a 1.7 M solution in pentante, 16.5 mmol) followed immediately by $ZnCl_2$ (8.25 mL of a 1 M solution in ether, 8.25 mmol). Let the solution warm to 0° C. and sit until enol triflate prepared as described below is ready. Cool a solution of preparation 6 (2.0 g, 5.49 mmol) in 55 mL of THF to −78° C. Add LiHMDS (6.6 mL of a 1 M solution in hexanes, 6.6 mmol). Stir for 45 min. Add via cannula a solution of N-(5-chloro-2-pyridyl)triflimide (2.59, 6.6 mmol) in 5 mL of THF. Warm to 0° C. and stir for 2 hrs. Dilute the solution with EtOAc, wash 2× with 1 M HCl, saturated aqueous sodium bicarbonate, and brine, dry over $Na_2SO_4$, filter, and concentrate. Add via cannula the solution of the aryl zinc described above to the enol triflate described above and $Pd(PPh_3)_4$ (634 mg, 0.55 mmol). Heat the solution to 60° C. for 1 hr. Cool the solution to room temperature, dilute with EtOAc, wash with saturated aqueous sodium bicarbonate, brine, dry over $Na_2SO_4$, filter and concentrate. Purify by silica gel flash chromatography (Biotage 40L column, 30-80% $CH_2Cl_2$/hexanes, over 60 min at 50 mL/min) to afford 1.13 g (2.13 mmol, 39%) of preparation 7. $^1$H NMR (400 MHz, $CDCl_3$) δ 7.76-7.72 (m, 2H), 7.50-7.35 (m, 11H), 7.09-7.06 (m, 2H), 6.97 (dd, 1H, J=1.3, 3.1 Hz), 5.15 (s, 2H), 5.10 (s, 2H), 5.11-5.02 (m, 2H), 4.00 (s, 3H), 3.95 (m, 1H), 3.54 (m, 1H), 3.40 (m, 1H), 3.12 (m, 1H), 2.50 (m, 1H).

PREPARATION 8

8-Benzyloxy-4-(4-benzyloxy-phenyl)-2-methylene-1,2,3,3a,4,9b-hexahydro-cyclopenta[c]chromene-6-carboxylic acid methyl ester (7)

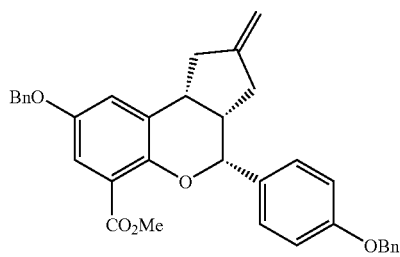

Add via cannula a solution of preparation 7 (1.10 g, 2.07 mmol) in 10 mL of $CH_2Cl_2$ to a solution of TFA (780 mg, 6.84 mmol) and $Et_3SiH$ (3.3 mL, 20.7 mmol) in 20 mL of $CH_2Cl_2$ at 0° C. Stir for 5 min and then quench with saturated aqueous sodium bicarbonate. Wash the organic solution two times with saturated aqueous sodium bicarbonate, dry over $Na_2SO_4$, filter, and concentrate. Purify by silica gel chromatography (Biotage 40M column, 50-100% $CH_2Cl_2$/hexanes over 60 min at 50 mL/min) to afford 800 mg (1.50 mmol, 73%) of preparation 8. $^1$H NMR (400 MHz, $CDCl_3$) δ 7.52-7.34 (m, 13H), 7.08-7.03 (m, 2H), 7.01 (d, 1H, J=3.1 Hz), 5.21 (d, 1H, J=1.8 Hz), 5.13 (s, 2H), 5.07 (s, 2H), 4.79-4.75 (m, 2H), 3.93 (s, 3H), 3.62 (d, 1H, J=7.5 Hz), 2.98-2.84 (m, 2H), 2.60 (d, 1H, J=16.3 Hz), 2.37 (m, 1H), 2.12 (d, 1H, J=17.1 Hz).

PREPARATION 9

8-Benzyloxy-4-(4-benzyloxy-phenyl)-6-methoxymethyl-2-methylene-1,2,3,3a,4,9b-hexahydro-cyclopenta[c]chromene (8)

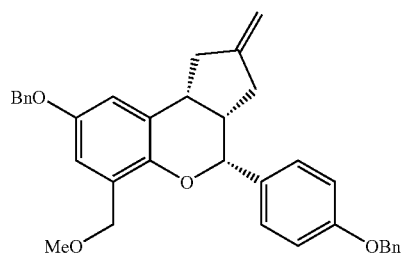

Add LAH (7.15 mL of 1 M solution in THF, 7.15 mmol) to a solution of preparation 8 (763 mg, 1.43 mmol) in 8 mL of THF at 0° C. Let the solution stir 2 hrs and quench with 10 mL of saturated aqueous ammonium chloride and 5 mL of 1 M NaOH. Dilute with EtOAc and stir 30 min. Separate and back extract the aqueous solution 2× with EtOAc. Wash the combined organic solutions with brine, dry over $Na_2SO_4$, filter and concentrate to yield 719 mg of the alcohol. To a solution of the alcohol (698 mg, 1.38 mmol) in 14 mL of THF at 0° C. add sodium hydride (110 mg of 60% dispersion in oil, 2.75 mmol). Let stir for 30 min and then add methyl iodide (0.17 mL, 2.73 mmol). Remove the cold bath and stir 2 hrs. Cool to 0° C. and quench with saturated aqueous ammonium chloride, dilute with EtOAc, wash with ½ bine, brine, dry over $Na_2SO_4$, filter, and concentrate. Purify by silica gel chromatography (40 g, 10-25% EtOAc/hexanes over 45 min at 35 mL/min) to afford 611 mg (1.18 mmol, 85%) of preparation 9. $^1$H NMR (400 MHz, $CDCl_3$) δ 7.51-7.33 (m, 12H), 7.07-7.03 (m, 2H), 6.97 (d, 1H, J=3.1 Hz), 6.76 (d, 1H, J=3.1 Hz), 5.15 (d, 1H, J=1.8 Hz), 5.13 (s, 2H), 5.07 (s, 2H), 4.80-4.72 (m, 2H), 4.60 (s, 2H), 3.60 (t, 1H, J=7.5 Hz), 3.47 (s, 3H), 2.93 (m, 1H), 2.77 (m, 1H), 2.64 (d, 1H, J=16.3 Hz), 2.39 (m, 1H), 2.09 (dd, 1H, J=7.9, 15.8 Hz).

PREPARATION 10

8-Benzyloxy-4-(4-benzyloxy-phenyl)-6-methoxymethyl-1,3a,4,9b-tetrahydro-3n-cyclopenta[c]chromen-2-one (9)

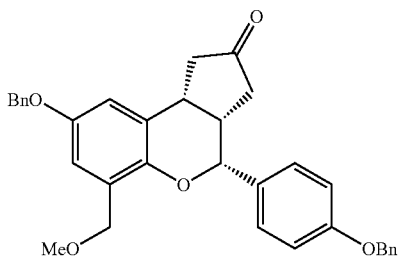

Add osmium tetroxide (0.73 mL of a 2.5 wt % solution in t-BuOH, 0.058 mmol) to a solution of preparation 9 (598 mg, 1.15 mmol), N-methylmorpholine (0.13 mL, 1.18 mmol), and N-methylmorpholine-N-oxide (270 mg, 2.30 mmol) in 10 mL of THF and 5 mL of water. Stir overnight and then add 5 mL of THF, 5 mL of water and sodium periodate (1.2 g, 5.61 mmol). Let stir 4 hrs. Quench with a 1:1 solution of saturated aqueous $Na_2SO_3$ and saturated aqueous $NaHCO_3$. Let stir 30 min. Separate and back extract the aqueous solution 2× with EtOAc. Wash the combined organic solutions with a 1:1 solution of saturated aqueous $Na_2SO_3$ and saturated aqueous $NaHCO_3$, brine, dry over $Na_2SO_4$, filter and concentrate. Purify by silica gel chromatography (40 g, 10-30% A/B, A=EtOAc, B=10% $CH_2Cl_2$ in hexanes) to afford 508 mg (0.976 mmol, 85%) of preparation 10. $^1$H NMR (400 MHz, $CDCl_3$) δ 7.50-7.34 (m, 12H), 7.06-7.03 (m, 2H), 7.02 (d, 1H, J=2.6 Hz), 6.71 (d, 1H, J=2.6 Hz), 5.17 (d, 1H, J=1.8 Hz), 5.13 (s, 2H), 5.06 (s, 2H), 4.60 (s, 2H), 3.91 (t, 1H, J=7.9 Hz), 3.47 (s, 3H), 2.99 (m, 1H), 2.81 (dd, 1H, J=8.4, 18.5 Hz), 2.63 (d, 1H, J=18.5 Hz), 2.32 (dd, 1H, J=12.3, 18.5 Hz), 2.04 (dd, 1H, J=7.9, 18.9 Hz).

PREPARATION 12

6-Bromo-8-methoxymethoxy-2-methylene-2,3,3a,9b-tetrahydro-1H-cyclopenta[c]chromen-4-one (11)

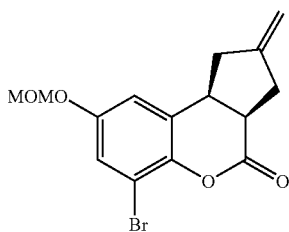

Preparation 12 is prepared from preparation 5 in a manner similar to preparation 6. $^1$H NMR (400 MHz, $CDCl_3$) δ 7.19 (d, 1H, J=3.0 Hz), 6.82 (d, 1H, J=3.0 Hz), 5.11 (d, 1H, J=7.0 Hz), 5.09 (d, 1H, J=6.6 Hz), 4.96-4.94 (m, 2H), 3.45 (s, 3H), 3.37 (dt, 1H, J=9.7, 7.0 Hz), 3.14-3.02 (m, 2H), 2.81-2.68 (m, 2H), 2.36 (m, 1H).

PREPARATION 13

6-Bromo-8-methoxymethoxy-4-(4-methoxymethoxy-phenyl)-2-methylene-1,2,3,9b-tetrahydro-cyclopenta[c]chromene (12)

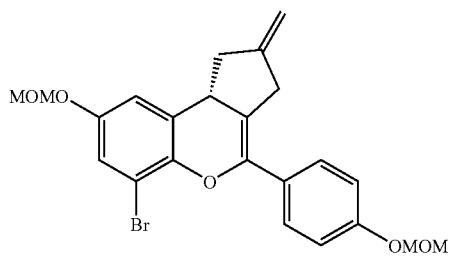

Preparation 13 is prepared from preparation 12 in a manner similar to preparation 7. $^1$H NMR (400 MHz, $CDCl_3$) δ 7.64-7.60 (m, 2H), 7.15 (dd, 1H, J=2.6, 0.9 Hz), 7.08-7.04 (m, 2H), 6.74 (dd, 1H, J=2.6, 0.9 Hz), 5.19 (s, 2H), 5.11 (d, 1H, J=10.0 Hz), 5.09 (d, 1H, J=10.0 Hz), 5.02 (bs, 1H), 4.95 (bs, 1H), 3.91 (t, 1H, J=10.1 Hz), 3.47 (s, 3H), 3.46 (s, 3H), 3.46 (m, 1H), 3.32 (m, 1H), 3.07 (dd, 1H, J=6.6, 13.6 Hz), 2.44 (m, 1H).

PREPARATION 14

6-Bromo-8-methoxymethoxy-4-(4-methoxymethoxy-phenyl)-2-methylene-1,2,3,3a,4,9b-hexahydro-cyclopenta[c]chromene (13)

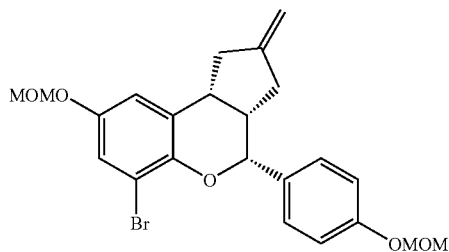

Preparation 14 is prepared from preparation 13 in a manner similar to preparation 8. $^1$H NMR (400 MHz, $CDCl_3$) δ 7.43-7.39 (m, 2H), 7.11 (dd, 1H, J=2.6, 0.9 Hz), 7.06-7.03 (m, 2H), 6.80 (dd, 1H, J=2.6, 0.9 Hz), 5.17 (s, 2H), 5.14 (d, 1H, J=1.8 Hz), 5.08 (d, 1H, J=10.5 Hz), 5.06 (d, 1H, J=10.5 Hz), 4.75 (bs, 1H), 4.74 (bs, 1H), 3.56 (t, 1H, J=7.5 Hz), 3.47 (s, 3H), 3.46 (s, 3H), 2.90 (m, 1H), 2.76 (m, 1H), 2.58 (d, 1H, J=16.3 Hz), 2.28 (m, 1H), 2.06 (dd, 1H, J=8.4, 16.7 Hz).

PREPARATION 15

6-Bromo-8-methoxymethoxy-4-(4-methoxymethoxy-phenyl)-1,3a,4,9b-tetrahydro-3H-cyclopenta[c]chromen-2-one (14)

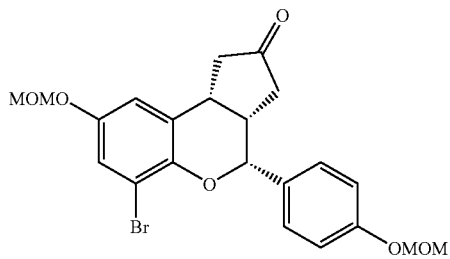

Preparation 15 is prepared from preparation 14 in a manner similar to preparation 10. $^1$H NMR (400 MHz, CDCl$_3$) δ 7.41-7.37 (m, 2H), 7.16 (dd, 1H, J=3.1, 0.9 Hz), 7.08-7.04 (m, 2H), 6.78 (dd, 1H, J=3.1, 0.9 Hz), 5.18 (s, 1H), 5.17 (s, 2H), 5.07 (d, 1H, J=10.1 Hz), 5.06 (d, 1H, J=10.1 Hz), 3.87 (t, 1H, J=7.0 Hz), 3.47 (s, 3H), 3.45 (s, 3H), 3.00 (m, 1H), 2.79 (ddd, 1H, J=1.3, 8.4, 18.5 Hz), 2.58 (d, 1H, J=18.5 Hz), 2.21 (dd, 1H, J=11.0, 18.0 Hz), 2.01 (dd, 1H, J=7.9, 18.5 Hz).

PREPARATION 16

6-Bromo-2,2-difluoro-8-methoxymethoxy-4-(4-methoxymethoxy-phenyl)-1,2,3,3a,4,9b-hexahydro-cyclopenta[c]chromene (15)

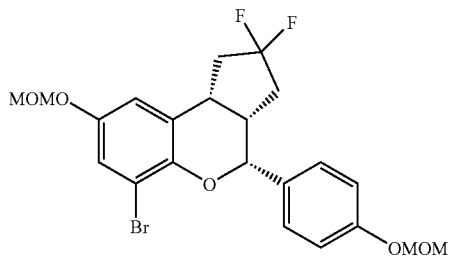

Stir a solution of preparation 15 (465 mg, 1.0 mmol) in 3 mL of (diethylamino)sulfur trifluoride and 3 mL of dichloroethane in a 16×150 mm culture tube at 40° C. overnight. Quench by adding the solution slowly to a stirring solution of 1:1 methylene chloride:saturated aqueous sodium bicarbonate. Separate and wash the organic solution with saturated aqueous sodium bicarbonate, brine, dry over Na$_2$SO$_4$, filter, and concentrate. Absorb the material to 4 g of silica gel and purify by silica gel chromatography (40 g, 0 to 20% A/B, A=EtOAc, B=10% CH$_2$Cl$_2$ in hexanes) to give 420 mg (0.86 mmol, 86%) of preparation 16. $^1$H NMR (400 MHz, CDCl$_3$) δ 7.43-7.39 (m, 2H), 7.17 (dd, 1H, J=2.6, 0.9 Hz), 7.10-7.16 (m, 2H), 6.77 (dd, 1H, J=2.6, 0.9 Hz), 5.19 (s, 2H), 5.11 (d, 1H, J=9.7 Hz), 5.09 (d, 1H, J=9.2 Hz), 5.06 (bs, 1H), 3.68 (dt, 1H, J=3.0, 8.8 Hz), 2.95 (ddt, 1H, J=2.6, 15.4, 7.9 Hz), 2.75 (m, 1H), 2.30 (dq, 1H, J=3.1, 15.4 Hz), 2.10 (m, 1H), 1.89 (m, 1H).

PREPARATION 17

2,2-Difluoro-8-methoxymethoxy-4-(4-methoxymethoxy-phenyl)-1,2,3,3a,4,9b-hexahydro-cyclopenta[c]chromene-6-carbonitrile (16)

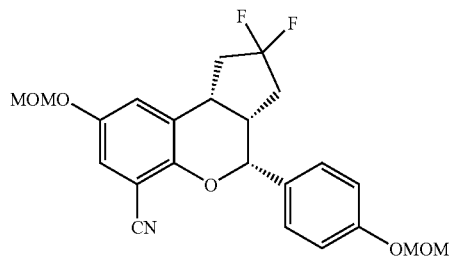

Add 0.5 mL of propionitrile to a 4 mL vial containing preparation 16 (24 mg, 0.05 mmol), copper(I) iodide (7 mg, 0.037 mmol), sodium cyanide (36 mg, 0.73 mmol), and Pd(PPh$_3$)$_4$ (21 mg, 0.018 mmol). Bubble nitrogen through the solution for 5 min, seal tightly, and warm to 90° C. with stirring overnight. Dilute the solution with EtOAc, wash with water, brine, dry over Na$_2$SO$_4$, filter, and concentrate. Adsorb the material to 500 mg of silica gel and purify by silica gel flash chromatography (4 g, 0-20% A/B, A=EtOAc, B=10% CH$_2$Cl$_2$ in hexanes) to afford 17 mg (0.034 mmol, 79%) of preparation 17. $^1$H NMR (400 MHz, CDCl$_3$) δ 7.37-7.33 (m, 2H), 7.14 (dd, 1H, J=0.9, 3.1 Hz), 7.07-7.03 (m, 2H), 7.02 (dd, 1H, J=0.9, 3.1 Hz), 5.17 (s, 2H), 5.11 (bs, 1H), 5.10 (d, 1H, J=8.4 Hz), 5.08 (d, 1H, J=8.4 Hz), 3.65 (t, 1H, J=7.0 Hz), 2.95 (ddt, 1H, J=2.2, 7.5, 14.9 Hz), 2.73 (m, 1H), 2.30 (m, 1H), 2.06 (m, 1H), 1.91 (m, 1H).

PREPARATION 18

2,2-Difluoro-8-methoxymethoxy-4-(4-methoxymethoxy-phenyl)-6-vinyl-1,2,3,3a,4,9b-hexahydro-cyclopenta[c]chromene (17)

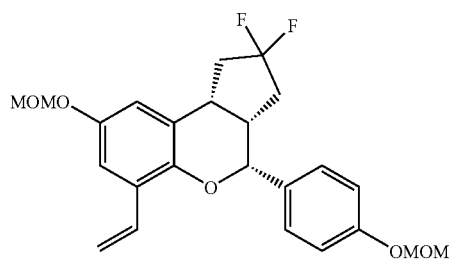

Add 0.45 mL of toluene, 0.1 mL of absolute ethanol, and vinylboronic acid dibutyl ester (0.030 mL, 0.136 mmol) to a 4 mL vial containing preparation 16 (30 mg, 0.062 mmol) and Pd(PPh$_3$)$_4$ (7 mg, 0.0061 mmol). Bubble nitrogen through the solution for 5 min, seal tightly, and warm to 80° C. with stirring overnight. Dilute the solution with EtOAc and wash with brine. Back extract the aqueous solution with EtOAc. Wash the combined organic solutions with brine, dry over Na$_2$SO$_4$, filter, and concentrate. Adsorb the material to 500 mg of silica gel and purify by silica gel flash chromatography (4 g, 0-20% A/B, A=EtOAc, B=10% CH$_2$Cl$_2$ in hexanes) to afford 12 mg (0.028 mmol, 45%) of preparation 18. $^1$H NMR (400 MHz, CDCl$_3$) δ 7.38-7.33 (m, 2H), 7.14-7.05 (m, 4H), 6.74 (d, 1H, J=2.6 Hz), 5.77 (dd, 1H, J=1.3, 18.1 Hz), 5.28 (dd, 1H, J=1.3, 12.3 Hz), 5.20 (s, 2H), 5.15 (d, 1H, J=10.1 Hz), 5.13 (d, 1H, J=9.7 Hz), 5.02 (bs, 1H), 3.67 (dt, 1H, J=3.1, 11.0 Hz), 3.50 (s, 1H), 2.89 (m, 1H), 2.74 (m, 1H), 2.30 (m, 1H), 2.17 (m, 1H), 1.86 (m, 1H).

PREPARATION 19

2,2-Difluoro-8-methoxymethoxy-4-(4-methoxymethoxy-phenyl)-1,2,3,3a,4,9b-hexahydro-cyclopenta[c]chromen-6-ol (18)

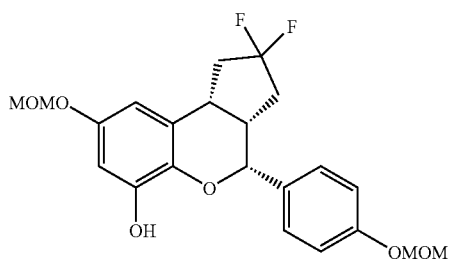

To a solution of preparation 16 (49 mg, 0.10 mmol) in 1 mL of THF at −78° C. add methyl lithium (0.032 mL of a 1.6 M solution in Et₂O, 0.05 mmol) followed by n-butyl lithium (0.126 mL of a 1.6 M solution in hexanes, 0.20 mmol). Stir the solution for 10 min and then add triisopropyl borate (0.070 mL, 0.30 mmol). Stir for the solution for 15 min and then add 0.1 mL of acetic acid and 0.1 mL of hydrogen peroxide. Stir the solution overnight. Dilute the solution with EtOAc, wash with brine, 1:1 brine:saturated aqueous sodium sulfite, saturated aqueous sodium bicarbonate, brine, dry over Na₂SO₄, filter and concentrate. Adsorb the material to 1.0 g of silica gel and purify by silica gel flash chromatography (10 g, 0-20% A/B, A=EtOAc, B=10% CH₂Cl₂ in hexanes) to afford 38 mg (0.090 mmol, 90%) of preparation 19. ¹H NMR (400 MHz, CDCl₃) δ 7.33-7.29 (m, 2H), 7.10-7.06 (m, 2H), 6.58 (d, 1H, J=2.6 Hz), 6.35 (d, 1H, J=2.6 Hz), 5.68 (s, 1H), 5.20 (s, 2H), 5.11 (d, 1H, J=12.8 Hz), 5.09 (d, 1H, J=12.8 Hz), 5.04 (bs, 1H), 3.64 (dt, 1H, J=2.6, 10.0 Hz), 3.50 (s, 3H), 3.48 (s, 3H), 2.84 (ddt, 1H, J=2.2, 12.3, 7.5 Hz), 2.73 (m, 1H), 2.35 (m, 1H), 2.19 (m, 1H), 1.90 (dt, 1H, J=7.5 14.5 Hz).

PREPARATION 20

[2,2-Difluoro-8-methoxymethoxy-4-(4-methoxymethoxy-phenyl)-1,2,3,3a,4,9b-hexahydro-cyclopenta[c]chromen-6-yl]-methanol (19)

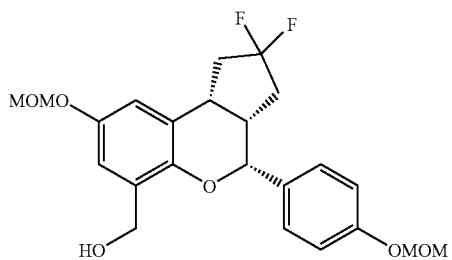

To a solution of preparation 16 (97 mg, 0.20 mmol) in 2 mL of THF at −78° C. add methyl lithium (0.062 mL of a 1.6 M solution in Et₂O, 0.10 mmol) followed by n-butyllithium (0.25 mL of a 1.6 M solution in hexanes, 0.40 mmol). Stir the solution for 15 min and then add DMF (0.077 mL, 1.0 mmol). Stir the solution for 30 min and then quench the reaction with saturated aqueous ammonium chloride. Let the solution warm to room temperature, separate; and back extract the aqueous solution with EtOAc. Wash the combined organic solutions with ½ brine, brine, dry over Na₂SO₄, filter and concentrate. Dissolve the material in 1 mL of THF and 1 mL of methanol. Add sodium borohydride (35 mg, 0.93 mmol). Let the solution stir for 30 min and quench the reaction with saturated aqueous ammonium chloride. Dilute the solution with EtOAc, wash with brine, dry over Na₂SO₄, filter and concentrate. Adsorb the material to silica gel and purify by silica gel flash chromatography (10 g, 0-30% A/B, A=EtOAc, B=10% CH₂Cl₂ in hexanes) to afford 68 mg (0.16 mmol, 87%) of preparation 20. ¹H NMR (400 MHz, CDCl₃) δ 7.32-7.27 (m, 2H), 7.03-7.07 (m, 2H), 6.91 (d, 1H, J=2.6 Hz), 6.72 (d, 1H, J=2.6 Hz), 5.17 (s, 2H), 5.11 (d, 1H, J=10.5 Hz), 5.09 (d, 1H, J=10.1 Hz), 5.03 (bs, 1H), 4.73 (dd, 1H, J=6.6, 13.2 Hz), 4.68 (dd, 1H, J=6.6, 13.2 Hz), 3.66 (dt, 1H, J=3.5, 8.8 Hz), 3.47 (s, 3H), 3.46 (s, 3H), 2.86 (ddt, 1H, J=2.2, 10.1, 7.5 Hz), 2.72 (m, 1H), 2.31 (m, 1H), 2.18 (t, 1H, J=6.6 Hz), 2.13 (m, 1H), 1.86 (dt, 1H, J=7.5, 14.5 Hz).

PREPARATION 21

2,2-Difluoro-8-methoxymethoxy-4-(4-methoxymethoxy-phenyl)-6-methoxymethyl-1,2,3,3a,4,9b-hexahydro-cyclopenta[c]chromene (20)

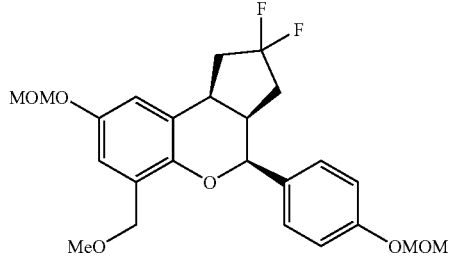

To a solution of preparation 20 (411 mg, 0.94 mmol) in 10 mL of THF at 0° C. add sodium hydride (75 mg of 60% dispersion in oil, 1.88 mmol). Let stir for 15 min and then add methyl iodide (0.12 mL, 1.92 mmol). Let the solution warm slowly to room temperature and stir overnight. Add another portion of sodium hydride (75 mg of 60% dispersion in oil, 1.88 mmol) and methyl iodide (0.12 mL, 1.92 mmol) and let stir for 4 hrs. Quench with saturated aqueous ammonium chloride, dilute with EtOAc, separate, back extract with EtOAc, wash combined organic solutions with brine, dry over Na₂SO₄, filter, and concentrate. Purify by silica gel chromatography (Biotage 40S column, 10:90:0 to 10:65:25 ratio CH₂Cl₂:hexanes:EtOAc over 60 min at 50 mL/min) to afford 384 mg (0.85 mmol, 91%) of preparation 21. ¹H NMR (400 MHz, CDCl₃) δ 7.34-7.29 (m, 2H), 7.07-7.03 (m, 2H), 6.97 (dd, 1H, J=3.1 Hz), 6.71 (dd, 1H, J=3.1 Hz), 5.17 (s, 2H), 5.12 (d, 1H, J=6.6 Hz), 5.09 (d, 1H, J=6.6 Hz), 4.99 (bs, 1H), 4.54 (d, 1H, J=12.7 Hz), 4.50 (d, 1H, J=12.7 Hz), 3.65 (dt, 1H, J=3.1, 9.7 Hz), 3.48 (s, 3H), 3.46 (s, 3H), 3.42 (s, 3H), 2.86 (ddt, 1H, J=2.6, 12.3, 7.9 Hz), 2.70 (m, 1H), 2.29 (m, 1H), 2.10 (m, 1H), 1.82 (dt, 1H, J=7.9, 14.9 Hz).

PREPARATION 22

2,2-Difluoro-8-methoxymethoxy-4-(4-methoxymethoxy-phenyl)-6-methyl-1,2,3,3a,4,9b-hexahydro-cyclopenta[c]chromene (20)

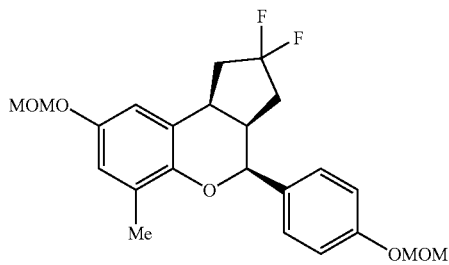

To a solution of Preparation 21 (192 mg, 0.43 mmol) in 2 mL of THF add a suspension of 70 mg of 10% Pd/C in 2 mL of iPrOH. Flush the solution with hydrogen at 60 psi. Let the solution stir 2 hrs. Filter the solution and concentrate. Purify by silica gel flash chromatography (40 g, 0-30% A/B, A=EtOAc, B=10% CH$_2$Cl$_2$ in hexanes) to afford 128 mg (0.30 mmol, 71%) of Preparation 22. $^1$H NMR (400 MHz, CDCl$_3$) δ 7.39-7.34 (m, 2H), 7.09-7.05 (m, 2H), 6.75 (d, 1H, J=3.1 Hz), 6.63 (d, 1H, J=2.6 Hz), 5.20 (s, 2H), 5.12 (d, 1H, J=6.6 Hz), 5.09 (d, 1H, J=6.6 Hz), 5.00 (bs, 1H), 3.66 (dt, 1H, J=3.5, 9.7 Hz), 3.50 (s, 3H), 3.49 (s, 3H), 2.89 (ddt, 1H, J=2.6, 12.7, 7.9 Hz), 2.73 (m, 1H), 2.31 (m, 1H), 2.26 (s, 3H), 2.1.3 (m, 1H), 1.84 (dt, 1H, J=7.0, 14.5 Hz).

EXAMPLE 1

8-Hydroxy-4-(4-hydroxy-phenyl)-6-methyl-1,3a,4,9b-tetrahydro-3H-cyclopenta[c]chromen-2-one

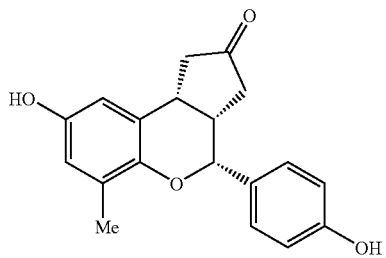

To a solution of preparation 10 (57 mg, 0.11 mmol) in 1 mL of THF add a suspension of 20 mg 10% Pd/C in 1 mL of iPrOH. Flush the solution with hydrogen at room pressure. Let the solution stir 1 hr. Filter the solution and concentrate. Adsorb the material to 500 mg of silica gel and purify by silica gel flash chromatography (4 g, 30-60% A/B, A=10% MeOH in EtOAc, B=hexanes) to afford Example 1. HRMS calc. for C$_{19}$H$_{19}$O$_4$: 311.1283; found: 311.1263 (M+H).

EXAMPLE 2

8-Hydroxy-4-(4-hydroxy-phenyl)-6-methoxymethyl-1,3a,4,9b-tetrahydro-3H-cyclopenta[c]chromen-2-one

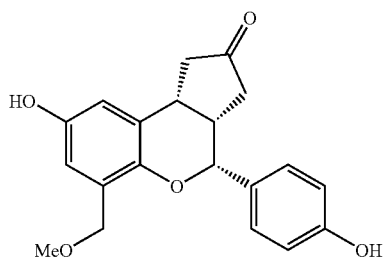

To a solution of preparation 10 (26 mg, 0.05 mmol) in 0.5 mL of THF add a suspension of 6 mg 5% Pd/C in 0.5 mL of iPrOH. Flush the solution with hydrogen at room pressure. Let the solution stir 4 hrs. Follow the reaction carefully by TLC to avoid over-reduction. Filter the solution and concentrate. Adsorb the material to 500 mg of silica gel and purify by silica gel flash chromatography (4 g, 30-60% A/B, A=10% MeOH in EtOAc, B=hexanes) to afford Example 2. HRMS calc. for C$_{20}$H$_{20}$O$_5$Na: 363.1209; found: 363.1245 (M+Na).

EXAMPLE 3

2,2-Difluoro-4-(4-hydroxy-phenyl)-6-methyl-1,2,3,3a,4,9b-hexahydro-cyclopenta[c]chromen-8-ol

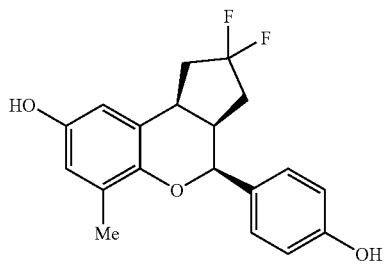

Example 3 is prepared from preparation 2' in a manner similar to example 5. The two enantiomers were separated by chiral preparative HPLC (Chiralpak AD, iPrOH/Heptane).

Enantiomer A: $^1$H NMR (400 MHz, MeOD): δ 7.24-7.28 (m, 2H), 6.76-6.80 (m, 2H), 6.46 (d, 1H, J=2.6 Hz), 6.38 (d, 1H, J=2.6 Hz), 4.90 (bs, 1H), 3.60 (t, 1H, J=7.5 Hz), 2.88 (m, 1H), 2.66 (m, 1H), 2.22 (m, 1H), 2.17 (s, 3H), 2.02 (m, 1H), 1.72 (m, 1H). HPLC (Chiralpak AD, 60/40 Heptane/i-PrOH; 1 mL/min; t$_R$=4.0 min). LRMS: 331.2 (M−H).

Enantiomer B; $^1$H NMR (400 MHz, MeOD): δ 7.24-7.28 (m, 2H), 6.76-6.80 (m, 2H), 6.46 (d, 1H, J=3.1 Hz), 6.38 (d, 1H, J=3.1 Hz), 4.90 (bs, 1H), 3.60 (t, 1H, J=6.2 Hz), 2.88 (ddt, 1H, J=2.2, 11.8, 7.5 Hz), 2.66 (m, 1H), 2.22 (m, 1H), 2.17 (s, 3H), 2.02 (m, 1H), 1.72 (m, 1H). HPLC (Chiralpak AD, 60/40 Heptane/i-PrOH; 1 mL/min; t$_R$=5.1 min). LRMS: 331.2 (M−H).

EXAMPLE 4

2,2-Difluoro-4-(4-hydroxy-phenyl)-6-methoxymethyl-1,2,3,3a,4,9b-hexahydro-cyclopenta[c]chromen-8-ol

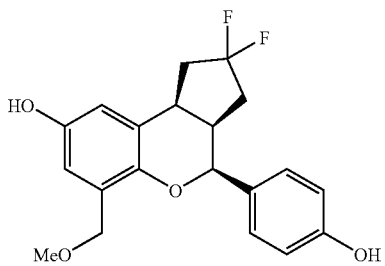

Example 4 is prepared from preparation 21 in a manner similar to example 5. The two enantiomers were separated by chiral preparative HPLC (Chiralpak AD, iPrOH/Heptane).

Enantiomer A: $^1$H NMR (400 MHz, MeOD): δ 7.23-7.27 (m, 2H), 6.76-6.80 (m, 2H), 6.66 (d, 1H, J=2.6 Hz), 6.52 (d, 1H, J=3.1 Hz), 4.94 (bs, 1H), 4.50 (d, 1H, J=11.9 Hz), 4.45 (d, 1H, J=12.3 Hz), 3.62 (t, 1H, J=8.4 Hz), 3.37 (s, 3H), 2.89 (m, 1H), 2.68 (m, 1H), 2.24 (m, 1H), 2.05 (m, 1H), 1.73 (m, 1H). HPLC (Chiralpak AD, 60/40 Heptane/i-PrOH; 1 mL/min; $t_R$=3.8 min). LRMS: 361.12 (M–H).

Enantiomer B: $^1$H NMR (400 MHz, MeOD): δ 7.23-7.27 (m, 2H), 6.76-6.80 (m, 2H), 6.66 (d, 1H, J=2.2 Hz), 6.52 (d, 1H, J=2.6 Hz), 4.94 (bs, 1H), 4.50 (d, 1H, J=12.3 Hz), 4.45 (d, 1H, J=11.9 Hz), 3.62 (t, 1H, J=8.8 Hz), 3.37 (s, 3H), 2.89 (m, 1H), 2.68 (m, 1H), 2.24 (m, 1H), 2.05 (m, 1H), 1.73 (m, 1H). HPLC (Chiralpak AD, 60/40 Heptane/i-PrOH; 1 mL/min; $t_R$=5.5 min). LRMS: 361.13 (M–H).

EXAMPLE 5

8-Hydroxy-4-(4-hydroxy-phenyl)-6-methoxymethyl-1,3a,4,9b-tetrahydro-3H-cyclopenta[c]chromen-2-one

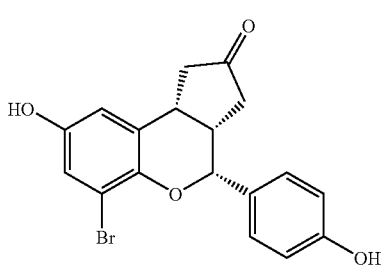

To a solution of preparation 15 (25 mg, 0.054 mmol) in 0.5 mL of THF add 0.25 mL of 5 M aqueous HCl. Let the solution stir overnight. Dilute with EtOAc and a little MeOH for solubility and wash with saturated aqueous sodium bicarbonate. Back extract the aqueous solution with 5% MeOH in EtOAc. Dry the combined organic solutions over $Na_2SO_4$, filter and concentrate. Adsorb the material to 500 mg of silica gel and purify by silica gel flash chromatography (4 g, 30-60% A/B, A=10% MeOH in EtOAc, B=hexanes) to afford Example 5. HRMS calc. for $C_{18}H_{14}BrO_4$: 375.0055; found: 375.0032 (M–H).

EXAMPLE 6

6-Bromo-2,2-difluoro-4-(4-hydroxy-phenyl)-1,2,3,3a,4,9b-hexahydro-cyclopenta[c]chromen-8-ol

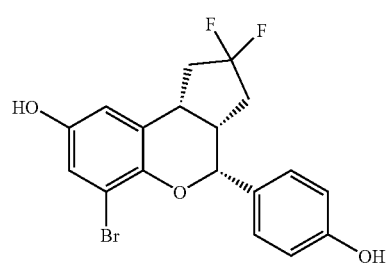

Example 6 is prepared from preparation 16 in a manner similar to example 5. HRMS calc. for $C_{18}H_{14}BrF_2O_4$: 395.0095; found: 395.0107 (M–H).

EXAMPLE 7

2,2-Difluoro-8-hydroxy-4-(4-hydroxy-phenyl)-1,2,3,3a,4,9b-hexahydro-cyclopenta[c]chromene-6-carbonitrile

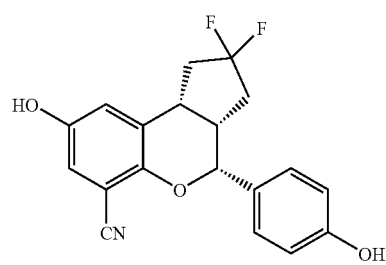

Example 7 is prepared from preparation 17 in a manner similar to example 5. HRMS calc. for $C_{19}H_{14}F_2NO_3$: 342.0942; found: 342.0946 (M–H).

EXAMPLE 8

2,2-Difluoro-4-(4-hydroxy-phenyl)-6-vinyl-1,2,3,3a,4,9b-hexahydro-cyclopenta[c]chromen-8-ol

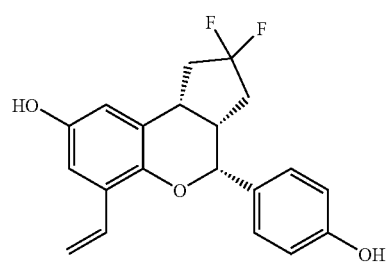

Example 8 is prepared from preparation 18 in a mariner similar to example 5. HRMS calc. for $C_{20}H_{19}F_2O_3$: 345.1302; found: 345.1325 (M+1).

EXAMPLE 9

2,2-Difluoro-4-(4-hydroxy-phenyl)-1,2,3,3a,4,9b-hexahydro-cyclopenta[c]chromene-6,8-diol

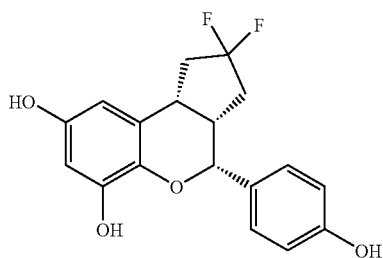

To a solution of preparation 19 in 2 mL of methanol add 500 mg of Dowex® 50WX2-200 acidic ion exchange resin. Stir the solution slowly overnight. Filter the solution and wash the resin with methanol. Concentrated the combined filtrates and adsorb the material to silica gel. Purify by silica gel flash chromatography (4 g, 15-70% A/B, A=10% MeOH in EtOAc, B=hexanes) to afford example 9. HRMS calc. for $C_{18}H_{17}F_2O_4$: 335.1095; found: 335.1114 (M+H).

EXAMPLE 10

[2,2-Difluoro-8-hydroxy-4-(4-hydroxy-phenyl)-1,2,3,3a,4,9b-hexahydro-cyclopenta[c]chromen-6-yl]-acetonitrile

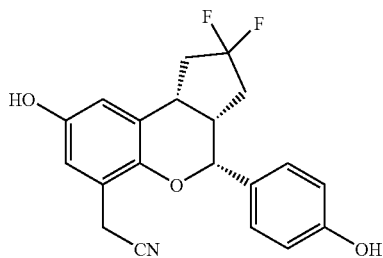

To a solution of preparation 20 (58 mg, 0.132 mmol) and triphenyl phosphine (175 mg, 0.67 mmol) and acetone cyanohydrin (0.125 mL, 1.37 mmol) in 1 mL of THF at 0° C. add dropwise via syringe diisopropylazodicarboxylate (0.13 mL, 0.66 mmol). Let the solution warm slowly to room temperature overnight. Concentrate the solution, adsorb the material to silica gel, and purify by silica gel flash chromatography (10 g, 0-30% A/B, A=EtOAc, B=10% $CH_2Cl_2$ in hexanes). Dissolve the material in 2 mL of THF and add 1 mL of 5 M aqueous HCl. Stir the solution overnight. Dilute the solution with EtOAc and a little methanol for solubility, wash with saturated aqueous sodium bicarbonate, brine, dry over $Na_2SO_4$, filter and concentrate. Adsorb the material to silica gel and purify by silica gel flash chromatography (4 g, 10-60% A/B, A=10% methanol in EtOAc, B=hexanes) to afford example 10. HRMS calc. for $C_{20}H_{17}F_2NNaO_3$: 380.1074; found: 380.1060 (M+Na).

EXAMPLE 11

2,2-Difluoro-4-(4-hydroxy-phenyl)-6-hydroxymethyl-1,2,3,3a,4,9b-hexahydro-cyclopenta[c]chromen-8-ol

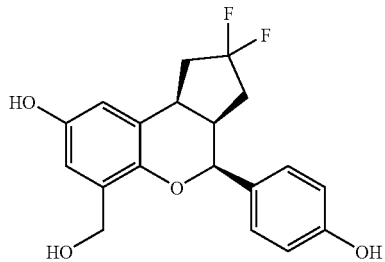

Example 11 is prepared from preparation 20 in a manner similar to example 5. $^1H$ NMR (400 MHz, $CD_3OD$) δ 7.28-7.24 (m, 2H), 6.80-6.76 (m, 2H), 6.74 (d, 1H, J=3.1 Hz), 6.49 (d, 1H, J=3.1 Hz), 4.94 (bs, 1H), 4.66 (d, 1H, J=13.6 Hz), 4.61 (d, 1H, J=13.6 Hz), 3.62 (d, 1H, J=7.5 Hz), 2.88 (d, 1H, J=2.2, 7.9 Hz), 2.68 (m, 1H), 2.24 (m, 1H), 2.06 (m, 1H), 1.73 (m, 1H), LRMS: 347.2 (M-H).

Test Procedures

ER Binding Assay

The competition ER binding assay is run in a buffer containing 50 mM N-[2-hydroxyethyl]piperazine-N'-[2-ethanesulfonic acid (Hepes) pH 7.5, 1.5 mM EDTA, 150 mM NaCl, 10% glycerol, 1 mg/mL ovalbumin, 5 mM DTT, 0.025 µCi per well of $^3$H-Estradiol(NEN #NET517 at 118 Ci/mmol, 1 mCi/mL), and 10 ng/well ER-α or ER-β Receptor (PanVera). Competing compounds are added at 10 different concentrations. Non-specific binding is determined in the presence of 1 µM of E2 (17-β Estradiol, Sigma, St. Louis, Mo.). The binding reaction (140 µL) is incubated for 4 hours at room temperature, then 70 µL of cold dextran coated charcoal (DCC) buffer is added to each reaction (DCC buffer is prepared by adding 0.75 g of charcoal [Sigma] and 0.25 g of dextran [Pharmacia] per 50 mL of assay buffer). The incubation plates are mixed for 8 minutes on an orbital shaker at 4° C. and then centrifuged at 3,000 rpm for 10 minutes at 4° C. An aliquot of 120 µl of the mix is transferred to another 96-well, white flat bottom plate (Costar) and 175 µl of Wallac Optiphase Hisafe 3 scintillation fluid is added to each well. The plates are sealed and then shaken vigorously on an orbital shaker. After an incubation of 2.5 hrs, the radioactivity is counted in a Wallac Microbeta counter. The $IC_{50}$ and percent inhibition at 10 µM are calculated. The $K_d$ for $^3$H-Estradiol is determined by saturation binding to ER-α and ER-β receptors. The $IC_{50}$ values for compounds are converted to $K_i$ values using the Cheng-Prusoff equation and the $K_d$ values are determined by saturation binding assay.

Preferred compounds bind to the ER-β receptor with a $K_i$ of less than 20 nM. More preferred compounds bind to the ER-β receptor with a $K_i$ of less than 1 nM. Compounds that are selective to binding to the ER-β receptor compared to the ER-α receptor bind to the ER-β receptor with a lower $K_i$ compared to the $K_i$ for the ER-α receptor.

As determined by the above assay, the compounds of examples 1-11 exhibit binding affinities (Ki) at the ER-α subtype in the range approximately 4→1000 nM and to the ER-β subtype in the range of approximately 0.3-120 nM. Furthermore, it should be noted that the compound of Example 4, enantiomer A, herein exhibits a selectivity ratio (ER-α Ki/ER-β Ki) of 91. In contrast, Example 1 of published PCT application WO 03/044006 A1 has a selectivity ratio of 8.

ER Agonist Assay

The agonist activity of the compounds of the invention can also be determined from assay(s) described in Harris, H. A.; Katzenellenbogen, J. A.; Katzenellenbogen, B. S. Endocrinology, 143, p. 4172-4177 (2002).

LNCaP Human PCa Xenograft Assay

ER-β agonists are evaluated for their effects on the growth of androgen-sensitive LNCaP human prostatic cancer (PCa) xenografts grown in intact sexually mature (5-6 weeks old) Hsd: Athymic Nude-nu (Athymic Nude) male mice. $2.0 \times 10^6$ LNCaP tumor cells are injected bilaterally by the subcutaneous route into the pre-tracheal region of testicular intact male mice. Mice are castrated via the scrotal route to serve as the positive control group. Test compounds are administered once per day by subcutaneous or gavage administration at multiple dose levels in a volume of 0.2 ml to xenograft-bearing mice starting on the day following tumor injection. Test compounds are reformulated weekly based on average group mean body weights. The vehicle for these studies is 1% carboxymethyl cellulose (CMC) with 0.25% Tween 80. Body weights and tumor measurements are recorded on a weekly basis and entered directly into a JMP™ (SAS; Cary, N.C.) spreadsheet from electronic caliper measurement. Tumor volumes in $mm^3$ are calculated in JMP using the following formula: L×W×H×0.5236. Tumor and body weight responses for individual mice are recorded on a weekly basis. When LNCaP tumor volumes enter log-phase expansion, lesions are measured every 3-4 days. Growth rates are determined using linear modeling of the log tumor values and time-to-treatment failure (tumor vol=1300-1500 $mm^3$) are determined using a linear extrapolation model (SAS; Cary, N.C.). Because of humane animal use considerations, animals are sacrificed when their tumor volumes approach 1200-1400 $mm^3$. At necropsy, final tumor measurement and body weights are recorded and whole blood is obtained via cardiac puncture and allowed to clot on ice. Serum is transferred to appropriately labeled 0.5 ml Eppendorf micro tubes, and samples are stored at −80° C. for biomarker analysis.

Benign Prostatic Hypertrophy (BPH) Assay

A mouse BPH study is essentially performed as a modified version of the rat BPH study as described earlier (Eur J Endocrinol. 2004 April; 150(4):591-60313). Thirteen week CD-1 male mice are single caged and housed for 1 week and treated with vehicle or compounds at various daily doses, given orally in a 1% Carboxymethylcellulose (CMC)+ 0.25% Tween 80 in PBS, pH 6.8 formulation. At the end of the study, the animals are sacrificed using $CO_2$, followed by blood collection using cardiac puncture. The animals are then subjected to necropsy to collect intact ventral prostate, seminal vesicle and/or testes to measure organ wet weight changes between treatment groups. Significant lowering of ventral prostate weights compared to vehicle control is determined using the Dunnet's test. The plasma derived from these animals are used to measure hormone changes and subsequently compared to vehicle control. The prostate tissue is snap-cooled in RNA Later™ solution, and total RNA is obtained using the RNeasy kit (Qiagen Corp.). Specific Taqman primers (see list below) for SGP-2 or clusterin, 18S ribosomal RNA (Applied Biosystems, Foster City, Calif., Catalog #4310893E) and smooth muscle myosin heavy chain (derived from Genebank sequence for rat NM_013607) are used to quantify biomarker changes in these prostate tissues using real time PCR.

PCR Primers:

mouse SGP-2 gi 192149-61F CGCAGACCGGACTC-CAGAT mouse SGP-2 gi 192149-121R CCACGCACAGCAG-GAGAAT mouse SGP-2 TaqMan™ probe:

mouse SGP-2 gi 192149-81T CCAAGGAGGCCACGC-CATGAA

While the exemplified compounds of the present invention demonstrate significant lowering of ventral prostate weights compared to vehicle control according to this test, preferred compounds demonstrate a significant lowering in prostate weight at doses of 10 mg/kg/day or less.

Therapeutic Methods of Use and Dosages

The various diseases and conditions described herein are well known and appreciated by those skilled in the art. It is also recognized that one skilled in the art may affect the associated diseases and conditions by treating a patient presently afflicted with the diseases or conditions or by prophylactically treating a patient afflicted with the diseases or conditions with a therapeutically effective amount of the compounds of Formula I.

A therapeutically effective amount can be readily determined by the attending diagnostician, as one skilled in the art, by the use of conventional techniques and by observing results obtained under analogous circumstances. In determining the therapeutically effective amount, the dose, a number of factors are considered by the attending diagnostician, including, but not limited to: the species of mammal; its size, age, and general health; the specific disease involved; the degree of or involvement or the severity of the disease; the response of the individual patient; the particular compound administered; the mode of administration; the bioavailability characteristic of the preparation administered; the dose regimen selected; the use of concomitant medication; and other relevant circumstances.

A therapeutically effective amount of a compound of Formula I is expected to vary from about 0.001 milligram per kilogram of body weight per day (mg/kg/day) to about 100 mg/kg/day. Preferred amounts can be determined by one skilled in the art.

In effecting treatment of a patient afflicted with the diseases and conditions described above, a compound of Formula I can be administered in any form or mode which makes the compound bioavailable in a therapeutically effective amount, including oral, inhalation, and parenteral routes. For example, compounds of Formula I can be administered orally, by inhalation of an aerosol or dry powder, subcutaneously, intramuscularly, intravenously, transdermally, intranasally, rectally, topically, and the like. Oral or inhalation administration is generally preferred for treatment of respiratory diseases, e.g. asthma. One skilled in the art of preparing formulations can readily select the proper form and mode of administration depending upon the particular characteristics of the compound selected, the disease or condition state to be treated, the stage of the disease or condition, and other relevant circumstances. (Remington's Pharmaceutical Sciences, 18th Edition, Mack Publishing Co. (1990)).

The compounds of the present invention can be administered alone or in the form of a pharmaceutical composition in combination with pharmaceutically acceptable carriers or excipients, the proportion and nature of which are determined by the solubility and chemical properties of the compound selected, the chosen route of administration, and standard pharmaceutical practice. The compounds of the present invention, while effective themselves, may be formulated and administered in the form of their pharmaceutically acceptable salts, such as acid addition salts or base addition salts, for purposes of stability, convenience of crystallization, increased solubility and the like.

Pharmaceutical compositions of the compounds of Formula I are prepared in a manner well known in the pharmaceutical art. The carrier or excipient may be a solid, semi-solid, or liquid material, which can serve as a vehicle or medium for the active ingredient. Suitable carriers or excipients are well known in the art. The pharmaceutical composition may be adapted for oral, inhalation, parenteral, or topical use and may be administered to the patient in the form of tablets, capsules, aerosols, inhalants, suppositories, solution, suspensions, or the like.

The compounds of the present invention may be administered orally, for example, with an inert diluent or with an edible carrier. They may be enclosed in gelatin capsules or compressed into tablets. For the purpose of oral therapeutic administration, the compounds may be incorporated with excipients and used in the form of tablets, troches, capsules, elixirs, suspensions, syrups, wafers, chewing gums and the like. These preparations typically contain at least 4% of the compound of the present invention, the active ingredient, but may be varied depending upon the particular form and may conveniently be between 4% to about 70% of the weight of the unit. The amount of the compound present in compositions is such that a suitable dosage will be obtained. Preferred compositions and preparations according to the present invention may be determined by someone skilled in the art.

The tablets, pills, capsules, troches and the like may also contain one or more of the following adjuvants: binders such as microcrystalline cellulose, gum tragacanth or gelatin; excipients such as starch or lactose, disintegrating agents such as alginic acid, Primogel, corn starch and the like; lubricants such as magnesium stearate or Sterotex; glidants such as colloidal silicon dioxide; and sweetening agents such as sucrose or saccharin may be added or a flavoring agent such as peppermint, methyl salicylate or orange flavoring. When the dosage unit form is a capsule, it may contain, in addition to materials of the above type, a liquid carrier such as polyethylene glycol or a fatty oil. Other dosage unit forms may contain other various materials that modify the physical form of the dosage unit, for example, as coatings. Thus, tablets or pills may be coated with sugar, shellac, or other enteric coating agents. A syrup may contain, in addition to the present compounds, sucrose as a sweetening agent and certain preservatives, dyes and colorings and flavors. Materials used in preparing these various compositions should be pharmaceutically pure and non-toxic in the amounts used.

For the purpose of parenteral therapeutic administration, the compounds of the present invention may be incorporated into a solution or suspension. These preparations should contain at least 0.1% of a compound of the invention, but may be varied to be between 0.1 and about 50% of the weight thereof. The amount of the compound of Formula I present in such compositions is such that a suitable dosage will be obtained. Preferred compositions and preparations can be determined by one of ordinary skill in the art.

The compounds of the present invention may also be administered by inhalation, such as by aerosol or dry powder. Delivery may be by a liquefied or compressed gas or by a suitable pump system that dispenses the compounds of the present invention or a formulation thereof. Formulations for administration by inhalation of compounds of formula (I) may be delivered in single phase, bi-phasic, or tri-phasic systems. A variety of systems are available for the administration by aerosols of the compounds of formula (I). Dry powder formulations are prepared by either pelletizing or milling the compound of formula (I) to a suitable particle size or by admixing the pelletized or milled compound of formula (I) with a suitable carrier material, such as lactose and the like. Delivery by inhalation includes the necessary container, activators, valves, subcontainers, and the like. Preferred aerosols and dry powder formulations for administration by inhalation can be determined by one skilled in the art.

The compounds of the present invention may also be administered topically, and when done so the carrier may suitably comprise a solution, ointment or gel base. The base, for example, may comprise one or more of the following: petrolatum, lanolin, polyethylene glycols, bee wax, mineral oil, diluents such as water and alcohol, and emulsifiers and stabilizers. Topical formulations may contain a concentration of the Formula I or its pharmaceutical salt from about 0.1 to about 10% w/v (weight per unit volume).

The solutions or suspensions may also include one or more of the following adjuvants: sterile diluents such as water for injection, saline solution, fixed oils, polyethylene glycols, glycerin, propylene glycol or other synthetic solvents; antibacterial agents such as benzyl alcohol or methyl paraben; antioxidants such as ascorbic acid or sodium bisulfite; chelating agents such as ethylene diaminetetraacetic acid; buffers such as acetates, citrates or phosphates and agents for the adjustment of tonicity such as sodium chloride or dextrose. The parenteral preparation can be enclosed in ampules, disposable syringes or multiple dose vials made of glass or plastic.

We claim:

1. A compound 2,2-difluoro-4-(4-hydroxy-phenyl)-6-methoxymethyl-1,2,3,3a,4,9b-hexahydro-cyclopenta[c]chromen-8-ol

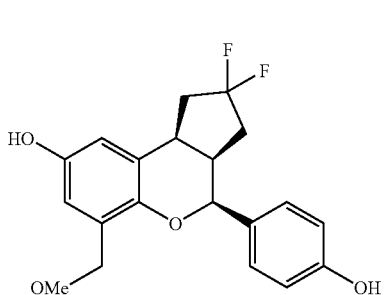

or a pharmaceutically acceptable salt thereof.

2. A pharmaceutical composition comprising a compound according to claim 1 and a pharmaceutically acceptable carrier, diluent or excipient.

3. Enantiomer A of 2,2-difluoro-4-(4-hydroxy-phenyl)-6-methoxymethyl-1,2,3,3a,4,9b-hexahydro-cyclopenta[c]chromen-8-ol

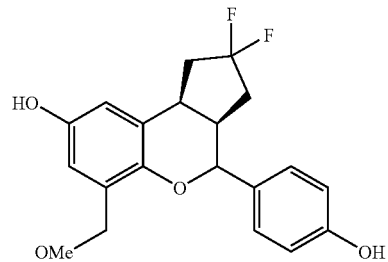

or a pharmaceutically acceptable salt thereof.

4. A pharmaceutical composition comprising a compound of claim 3 and a pharmaceutically acceptable carrier, diluent or excipient.

* * * * *

UNITED STATES PATENT AND TRADEMARK OFFICE
CERTIFICATE OF CORRECTION

| | | |
|---|---|---|
| PATENT NO. | : 7,354,951 B2 | Page 1 of 1 |
| APPLICATION NO. | : 11/574034 | |
| DATED | : April 8, 2008 | |
| INVENTOR(S) | : Bryan Hurst Norman et al. | |

It is certified that error appears in the above-identified patent and that said Letters Patent is hereby corrected as shown below:

On the Title Page:
Insert --(60) Related U.S. Application Data
Provisional Application No. 60/619,627 filed October 18, 2004--.

Col. 1, line 4 of the specification, insert the following
cross-reference after the title:
--This application is the national phase application, under 35 USC
371, for PCT/US2005/035472, filed October 5, 2005, which claims
the benefit, under 35 USC 119(e), of US provisional application
no. 60/619,627, filed October 18, 2004.--.

Signed and Sealed this

Twenty-third Day of November, 2010

David J. Kappos
*Director of the United States Patent and Trademark Office*